(12) United States Patent
Pahan

(10) Patent No.: US 11,279,754 B2
(45) Date of Patent: Mar. 22, 2022

(54) COMPOSITIONS AND METHODS FOR TREATING CANCER

(71) Applicant: RUSH UNIVERSITY MEDICAL CENTER, Chicago, IL (US)

(72) Inventor: Kalipada Pahan, Skokie, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 0 days.

(21) Appl. No.: 15/551,710

(22) PCT Filed: Mar. 4, 2016

(86) PCT No.: PCT/US2016/020864
§ 371 (c)(1),
(2) Date: Aug. 17, 2017

(87) PCT Pub. No.: WO2016/144743
PCT Pub. Date: Sep. 15, 2016

(65) Prior Publication Data
US 2018/0194837 A1  Jul. 12, 2018

Related U.S. Application Data

(60) Provisional application No. 62/131,343, filed on Mar. 11, 2015.

(51) Int. Cl.
*A61K 39/395*  (2006.01)
*C07K 16/24*   (2006.01)
*C07K 16/30*   (2006.01)

(52) U.S. Cl.
CPC .......... *C07K 16/244* (2013.01); *A61K 39/395* (2013.01); *C07K 16/3069* (2013.01); *C07K 2317/73* (2013.01); *C07K 2317/76* (2013.01)

(58) Field of Classification Search
None
See application file for complete search history.

(56) References Cited

U.S. PATENT DOCUMENTS 8,080,247 B2 * 12/2011 Giles-Komar ....... C12Q 1/6876
424/139.1
2014/0314710 A1  10/2014 Pahan

FOREIGN PATENT DOCUMENTS

WO  WO 2004/081190 A2  9/2004

OTHER PUBLICATIONS

De Genst et al., Dev Comp Immunol 2006; 30:187-98 (Year: 2006).*
Almagro & Fransson, Frontiers in Bioscience 2008; 13:1619-33 (Year: 2008).*
Yoshinaga et al., J. Biochem 2008; 143:593-601 (Year: 2008).*
Dasgupta et al. (Hybridoma 2008, vol. 27, No. 3, pp. 141-151). (Year: 2008).*
White et al. (2001, Ann. Rev. Med., 2001,52:125-145) (Year: 2001).*
Meibohm (Pharmacokinetics and Pharmacodynamics of Biotech Drugs, Wiley-VHC, 2006, chapters, p. 45-91) (Year: 2006).*
International Search Report and Written Opinion for PCT/US2016/020864 dated May 20, 2016, 10 pgs.
Dasgupta, Set al. "Generation of Functional Blocking Monoclonal Antibodies Against Mouse Interleukin-12 p40 Homodimerand Monomer" Hybidoma 2008, vol. 27, No. 3, pp. 141-151; p. 147, first column, first paragraph; p. 148, first column, first paragraph; p. 149, second column, second paragraph.
HeCKel, MC et al. "Human Breast Tumor Cells Express IL-10 and IL-12P40 Transcripts and Proteins, But do not Produce IL-12P70" Cellular Immunology 20•1, vol. 286, No. 2, pp. 143-153 (Abstract); Abstract.
Wheeler, RD et al. "Elevated Interferon Gamma Expression in the Central Nervous System of Tumour Necrosis Factor Receptor 1-Deficient Mice with Experimental Autimmune Encephalomyelitis" Immunology 2006, vol. 118, pp. 527-538; p. 527, seco.nd column, paragraph.
ABDI Ket al. "Free IL-12p40 Monomer is a Polyfuncliom,11 Adapter for Generating Novel IL-12-Like Heterodimers Extracellularly" J Immunol. Jun. 15, 2014, vol. 192, No. 12, pp. 6028-6036 (pp. 1-23); p. 7, second paragraph.
Hamza, T et al. "Interleukin 12 a Key Immunoregulatory Cytokine in Infection Applications" International Journal of Molecular Sciences 2010, vol. 11, ,.,ages 789-806; p. 790, fifth paragraph; p. 791, first paragraph.
Lin, WW & Karin M, "A cytokine-mediated link between innate immunity, inflammation, and cancer", *J Clin Invest.*, vol. 117, No. 5, pp. 1175-1183.
Trinchieri, G. "Interleukin-12: A Cytokine Produced by Antigen-Presenting Cells With Immunoregulatory Functions in the Generation of T-Helper Cells Type 1 and Cytotoxic Lymphocytes", *Blood*, vol. 84, No. 12, 1994, pp. 4008-4027.
Cui J, et al., "Requirement for $V_\alpha 14$ NKT Cells in IL-12-Mediated Rejection of Tumors", *Science*, vol. 278, 1997, pp. 1623-1626.
Zitvogel, L. et al., "Cancer immunotherapy of established tumor with IL-12. Effective delivery by genetically engineered fibroblasts", vol. 155, 1995, pp. 1393-1403.
Gately, M K, et al., "The Interleukin-12/Interleukin-12-Receptor System: Role in Normal and Pathologic Immune responses", *Annu Rev Immunol*, vol. 16, 1998, pp. 495-521.
Brahmachari, S., "Suppression of Regulatory T Cells by IL-12p40 Homodimer via Nitric Oxide", *J Immunol*, vol. 183, 2009, pp. 2045-2058.

(Continued)

*Primary Examiner* — Meera Natarajan
(74) *Attorney, Agent, or Firm* — Barnes & Thornburg LLP

(57) ABSTRACT

One aspect of the invention provides a method for treating a cancer including administering to a subject in need of such treatment a composition including a therapeutically effective amount of an antibody directed against p40 monomer or an immunologically active fragment thereof. In various embodiments, the antibody is a polyclonal, monoclonal, human, humanized, and chimeric antibody; a single chain antibody or an epitope-binding antibody fragment. In other embodiments, the cancer is, for example, prostate cancer, breast cancer or liver cancer.

14 Claims, 24 Drawing Sheets
Specification includes a Sequence Listing.

(56) References Cited

OTHER PUBLICATIONS

Jana, M., "Il-12 P40 Homodimer, the So-Called Biologically Inactive Molecule, Induces Nitric Oxide Synthase in Microglia via IL-12Rβ1", *GLIA*, vol. 57, 2009, pp. 1553-1565.

Pahan, K. et al., "Induction of Nitric-oxide Synthase and Activation of NF-κB by Interleukin-12 p40 in Microglial Cells", *J Biol Chem.*, vol. 276, No. 11, 2001, pp. 7899-7905.

Jana, M. et al., "IL-12 p40 homodimer, but not IL-12 p70, induces the expression of IL-16 in microglia and macrophages", *Mol Immunol.*, vol. 46, 2009, pp. 773-783.

Jana, M. et al., Induction of lymophotoxin-α by interleukin-12 p40 homodimer, the so-called biologically inactive molecule, but not IL-12 p70, *Immunology*, vol. 127, 2008, pp. 312-325.

Dasgupta, S. "Generation of Functional Blocking Monoclonal Antibodies Against Mouse interleukin-12 p40 Homodimerand Monomer", *HYBRIDOMA*, vol. 27 No. 3, 2008, pp. 141-151.

Mondal, S. et al., "Functional Blocking Monoclonal Antibodies against IL-12p40 Homodimer Inhibit Adoptive Transfer of Experimental Allergic Encephalomyelitis", *J Immunol*, vol. 182, 2009, pp. 5013-5023.

Nastala, CL., et al., "Recombinant IL-12 administration induces tumor regression in association with IFN-gamma production.", *J Immunol*, vol. 153, 1994, pp. 1697-1706.

Sato T et al., "Interleunkin 10 in the tumor microenvironment: a target for anticancer immunotherapy", *Immunol Res.*, vol. 51,2011, pp. 170-182.

Kopf, M. et al., "Disruption of the murine IL-4 gene blocks Th2 cytokine responses", *Nature*, vol. 362, 1993, pp. 245-248.

Hori S. et al. "Control of Regulatory T Cell Development by the Transcription Factor *Foxp3*", *Science*, vol. 299, 2003, pp. 1057-1061.

Wysocka. M. et al. "Interleukin-12 is required for interferon-y production and Tethality in lipopolysaccharide-induced shock in mice", *Eur J Immunol*, vol. 25, 1995, pp. 672-676.

Durali, D et al., "In human B cells IL-12 triggers a cascade of molecular events similar to Th1 commitment", *Blood*, vol. 102, 2003, pp. 4084-4089.

Tucker, JA et al., "Immunotherapy: Shifting the Balance of Cell-Mediated Immunity and Suppression in Human Prostrate Cancer", *Cancers*, vol. 4, 2012, pp. 1333-1348.

Ngiow, SF et al., "A balance of interleukin -12 and -23 in cancer", *Trends Immunol*, vol. 34, 2013, pp. 548-555.

Cua, DJ et al., "Interleukin-23 rather than interleukin-12 is the critical cytokine for autoimmune inflammation of the brain", Nature, vol. 421, 2003, pp. 744-748.

Selleck, WA. et al, "IFN-y Sensitization of Prostate Cancer Cells to FAS-Mediated Death: A Gene Therapy Approach", *Mol Ther*, vol. 7, No. 2, 2003, pp. 185-192.

Garcia-Tunon I. et al., "Influence of IFN-gamma and its receptors in human breast cancer", *BMC Cancer*, vol. 7, 2007, 11 pages.

Wall, L. et al. "IFN-γ Induces Apoptosis in Ovarian Cancer Cells in Vivo and In Vitro", *Clin Cancer Res*, vol. 9, 2003, pp. 2487-2496.

Cherwinski, HM et al. "Two Types of Mouse Helper T Cell Clone III. Further Differences in Lymphokine Synthesis between TH1 and TH2 Clones Revealed by RNA Hybridization, Functionally Monospecific Bioassays, and Monoclonal Antibodies", *J Exp Med*, vol. 166, 1987, pp. 1229-1244.

Tripp, CS et al., "Interleukin 12 and tumor necrosis factor α are costimulators of interferon γ production by natural killer cells in severe combined immunodeficiency mice with listerioisis, and interleukin 10 is a physiologic antagonist", *Proc Natl Acad Sci USA*, vol. 90, 1993, 3725-3729.

Fenton, MJ et al., "Induction of Gamma Interferon Production in Human Alveolar Macrophages by *Mycobacterium tuberculosis*", *Infect Immun*, vol. 65, No. 12, 1997, pp. 5149-5156.

Sharma, M et al., "Pulmonary epithelial cells are a source of Interferon-γ in Yesponse to *Mycobacterium tuberculosis* infection", *Immunol Cell Biol*, vol. 85, 2007, pp. 229-237.

Rouabhia, M et al., "Interleukin-18 and Gamma Interferon Production by Oral Epithelial Cells in Response to Exposure to *Candida albicans* or Lipopolysaccharide Stimulation", *Infect Immun*, vol. 70, No. 12, 2002, pp. 7073-7080.

Schroder, K et al., "Interferon-γ: an overview of signals, Mechanisms and functions", *J Leukoc Biol*, vol. 75, 2004, pp. 163-189.

Gollob, JA et al. "Altered Interleukin-12 Responsiveness in Th1 and Th2 Cells Is Associated With the Differential Activation of STAT5 and STAT1", *Blood*, vol. 91, No. 4, 1998, pp. 1341-1354.

Jana, M et al., "Gemfibrozil, a Lipid-lowering Drug, Increases Myelin Genes in Human Oligodendrocytes via Peroxisome Proliferator-activated Receptor-β*", *J Biol Chem*, vol. 287, No. 41, 2012, p. 34134-34148.

Khasnavi, S et al., "Cinnamon Treatment Upregulates Neuroprotective Proteins Parkin and DJ-1 and Protects Dopaminergic Neurons in a Mouse Model of Parkinson's Disease", *J Neuroimmune Pharmacol*, vol. 9, 2014, pp. 569-581.

Ghosh, A et al., "Selective inhibition of NF-κB activation prevents dopaminergic neuronal loss in a mouse model of Parkinson's disease", *Proc Natl Acad Sci USA*, vol. 104, No. 47, 2007, p. 18754-18759.

Corbett GT et al. "Gemfibrozil, a Lipid-Lowering Drug, Upregulates IL-1 Receptor Antagonist in Mouse Cortical Neurons: Implications for Neuronal Self-Defense", *J Immunol*, vol. 189, 2012, pp. 1002-1013.

Supplemental EP search report for European Patent Application No. 16762206.7 dated Aug. 23, 2018, 11 pgs.

Yamamoto, M et al., "TSU68 Prevents Liver 1-15 Metastasis of Colon Cancer Xenografts by Modulating the Premetastatic Niche", *Cancer Res*, vol. 68, No. 23, 2008, pp. 9754-9762.

Kundu, M et al. "Selective neutralization of IL-12 p40 monomer induces death in prostate cancer cells via Il-12-IFN-γ", *PNAS*, vol. 114, No. 43, 2017, p. 11482-11487.

[on-line] https://www.biolegend.com/en-gb/products/ultra-leaf-low-endotoxin--azide-free-purified-anti-mouse-il-12-il-23-p40-mnomer--dimer--heterodimer-antibody-7751; retrieved Jun. 24, 2020.

Heremans et al., "Role of Interferon-gamma and Nitric Oxide in Pulmonary Edema and Death Induced by Lipopolysaccharide," Am J Respir Grit Care Med., vol. 161, (2000), pp. 110-117.

\* cited by examiner

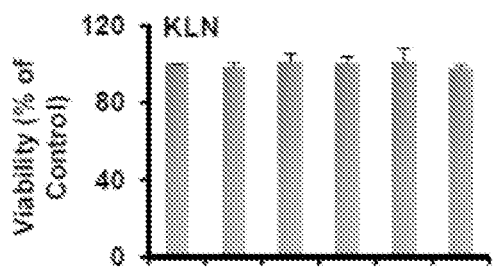
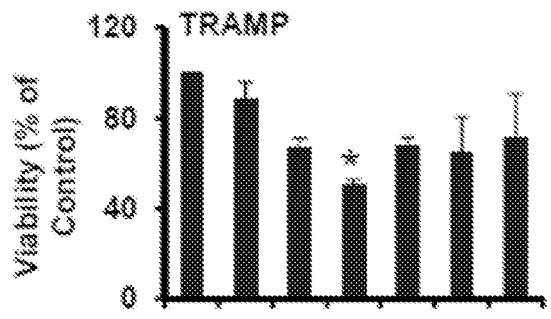
Fig. 2E
Fig. 2F
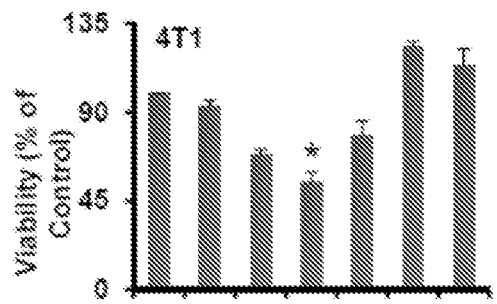
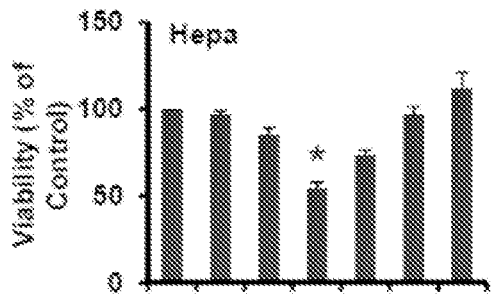
Fig. 2G
Fig. 2H
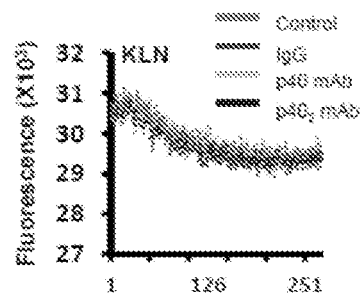
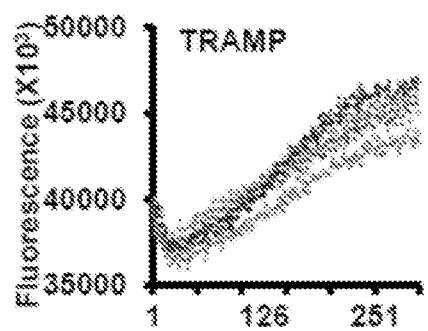
Fig. 2I
Fig. 2J

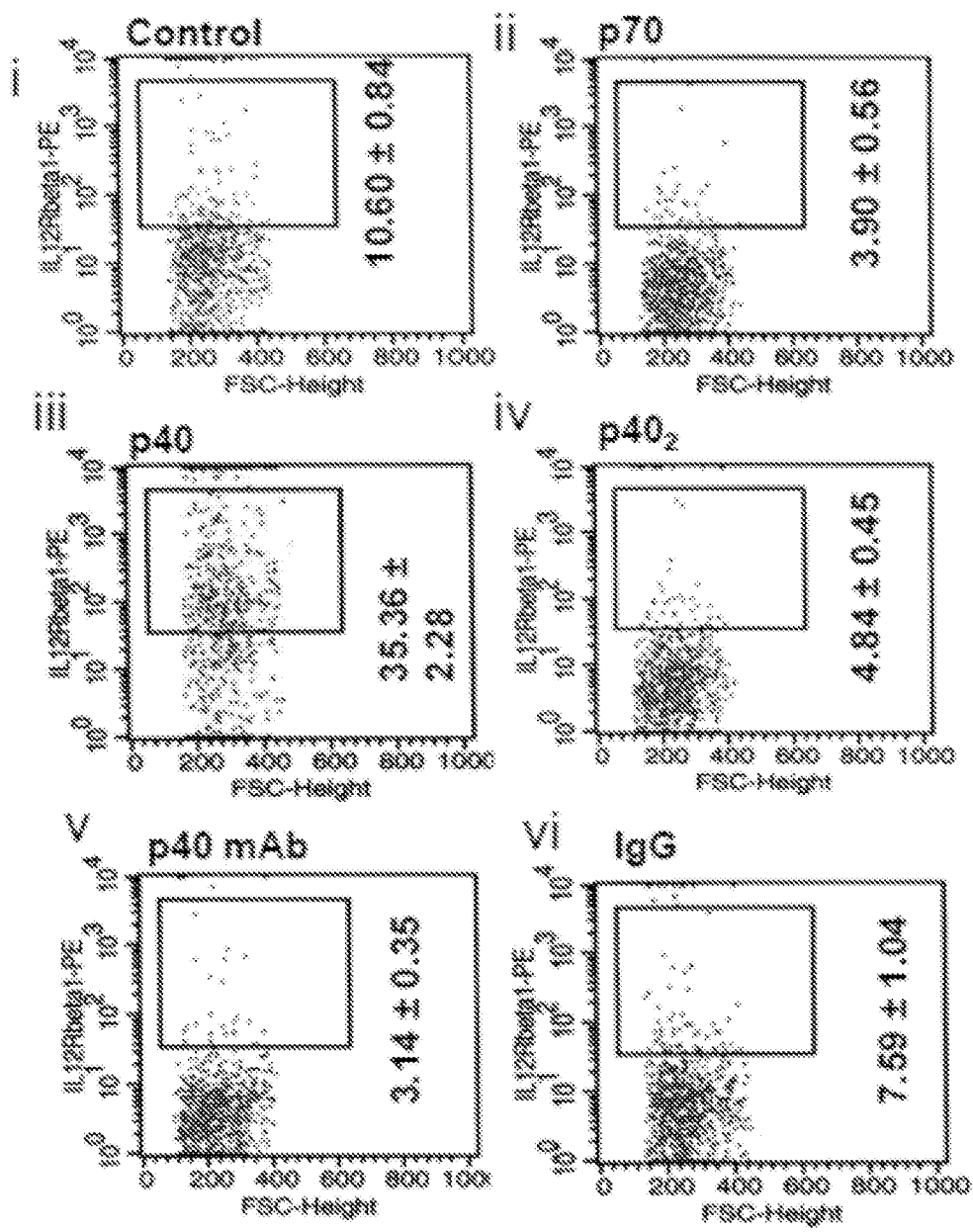
Figures 5Ai through 5Avi

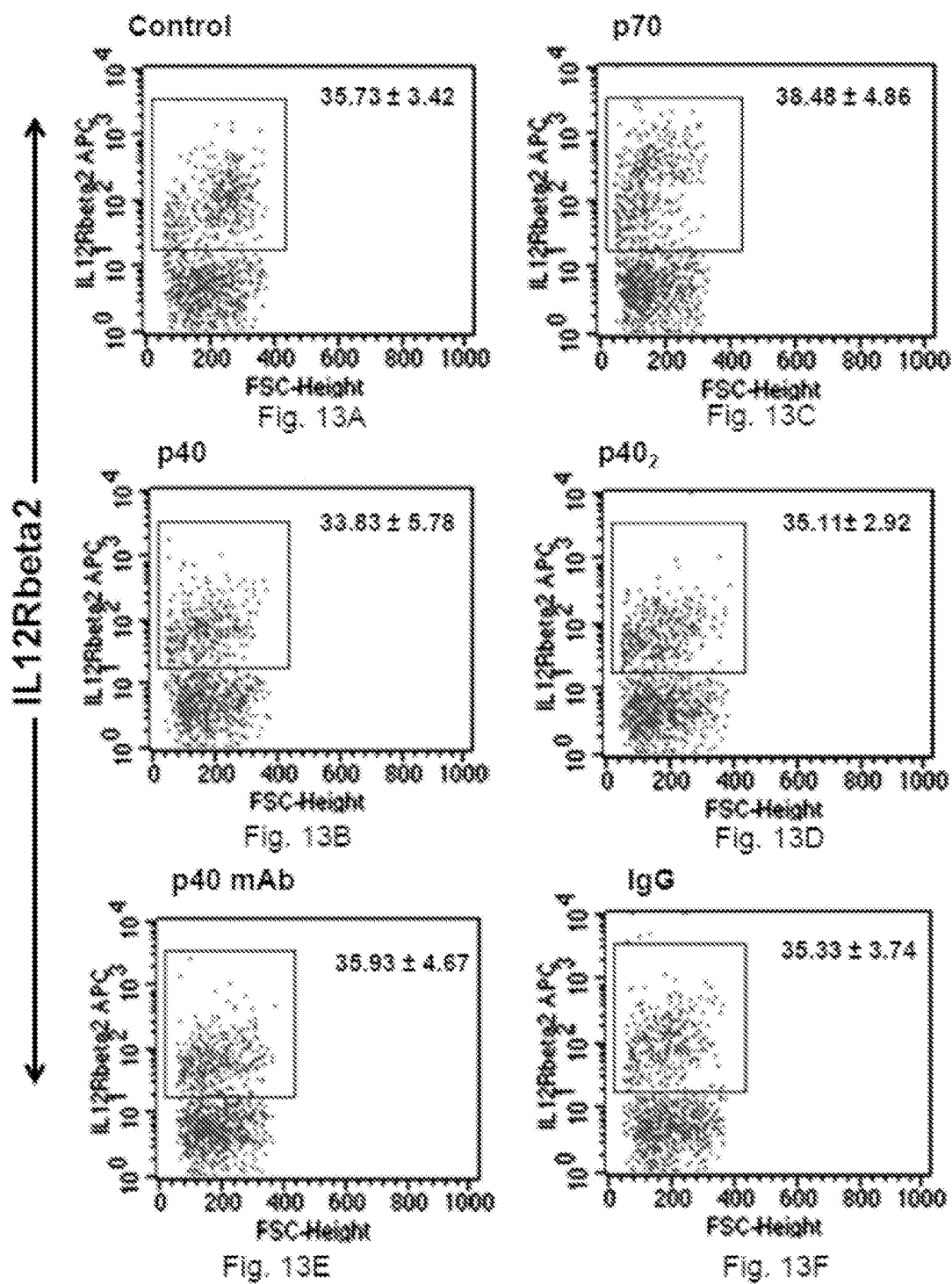

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Artificial mouse IFN gamma primer, sense strand

<400> SEQUENCE: 1
cggcacagtc attgaaagcc                                              20

<210> SEQ ID NO 2
<211> LENGTH: 20
<212> TYPE: DNA
<213> ORGANISM: Artificial Sequence
<220> FEATURE:
<223> OTHER INFORMATION: Artificial mouse IFN gamma primer, antisense
      strand

<400> SEQUENCE: 2
tgcatccttt ttcgccttgc                                              20

<210> SEQ ID NO 3
<211> LENGTH: 20
<212> TYPE: DNA
<213> ORGANISM: Artificial Sequence
<220> FEATURE:
<223> OTHER INFORMATION: Artificial mouse IL10 primer, sense strand

<400> SEQUENCE: 3
taaggctggc cacacttgag                                              20

<210> SEQ ID NO 4
<211> LENGTH: 20
<212> TYPE: DNA
<213> ORGANISM: Artificial Sequence
<220> FEATURE:
<223> OTHER INFORMATION: Artificial mouse IL10 primer, antisense strand

<400> SEQUENCE: 4
gttttcaggg atgaagcggc                                              20

<210> SEQ ID NO 5
<211> LENGTH: 20
<212> TYPE: DNA
<213> ORGANISM: Artificial Sequence
<220> FEATURE:
<223> OTHER INFORMATION: Artificial mouse Tbeta primer, sense strand

<400> SEQUENCE: 5
attggttgga gaggaagcgg                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Artificial mouse Tbeta primer, antisense strand

<400> SEQUENCE: 6
tgtgcaccct tcaaaccctt                                                  20

<210> SEQ ID NO 7
<211> LENGTH: 20
<212> TYPE: DNA
<213> ORGANISM: Artificial Sequence
<220> FEATURE:
<223> OTHER INFORMATION: Artificial mouse GATA3 primer, sense strand

<400> SEQUENCE: 7
tggcgccgtc ttgatagttt                                                  20

<210> SEQ ID NO 8
<211> LENGTH: 20
<212> TYPE: DNA
<213> ORGANISM: Artificial Sequence
<220> FEATURE:
<223> OTHER INFORMATION: Artificial mouse GATA3 primer, antisense strand

<400> SEQUENCE: 8
cctcttccgt cagcggatac                                                  20

<210> SEQ ID NO 9
<211> LENGTH: 20
<212> TYPE: DNA
<213> ORGANISM: Artificial Sequence
<220> FEATURE:
<223> OTHER INFORMATION: Artificial mouse Foxp3 primer, sense strand

<400> SEQUENCE: 9
tgtgcctggt atatgctccc                                                  20

<210> SEQ ID NO 10
<211> LENGTH: 20
<212> TYPE: DNA
<213> ORGANISM: Artificial Sequence
<220> FEATURE:
<223> OTHER INFORMATION: Artificial mouse Foxp3 primer, antisense strand

<400> SEQUENCE: 10
gttcttgtca gaggcaggct                                                  20

<210> SEQ ID NO 11
<211> LENGTH: 20
<212> TYPE: DNA
<213> ORGANISM: Artificial Sequence
<220> FEATURE:
<223> OTHER INFORMATION: Artificial mouse GAPDH primer, sense strand

<400> SEQUENCE: 11
gcatcttctt gtgcagtgcc                                                  20

<210> SEQ ID NO 12
<211> LENGTH: 20
<212> TYPE: DNA
<213> ORGANISM: Artificial Sequence
<220> FEATURE:
<223> OTHER INFORMATION: Artificial mouse GAPDH primer, antisense strand
```

```
<400> SEQUENCE: 12
tacggccaaa tccgttcaca                                               20

<210> SEQ ID NO 13
<211> LENGTH: 20
<212> TYPE: DNA
<213> ORGANISM: Artificial Sequence
<220> FEATURE:
<223> OTHER INFORMATION: Artificial mouse PDL-1 primer, sense strand

<400> SEQUENCE: 13
tcacttgcta cgggcgttta                                               20

<210> SEQ ID NO 14
<211> LENGTH: 20
<212> TYPE: DNA
<213> ORGANISM: Artificial Sequence
<220> FEATURE:
<223> OTHER INFORMATION: Artificial mouse PDL-1 primer, antisense strand

<400> SEQUENCE: 14
tgccaatcga cgatcagagg                                               20

<210> SEQ ID NO 15
<211> LENGTH: 20
<212> TYPE: DNA
<213> ORGANISM: Artificial Sequence
<220> FEATURE:
<223> OTHER INFORMATION: Artificial mouse PDL-2 primer, sense strand

<400> SEQUENCE: 15
ggtgtgtgat tggtaggcca                                               20

<210> SEQ ID NO 16
<211> LENGTH: 20
<212> TYPE: DNA
<213> ORGANISM: Artificial Sequence
<220> FEATURE:
<223> OTHER INFORMATION: Artificial mouse PDL-2 primer, antisense strand

<400> SEQUENCE: 16
catccagcag gtaaccaggg                                               20

<210> SEQ ID NO 17
<211> LENGTH: 20
<212> TYPE: DNA
<213> ORGANISM: Artificial Sequence
<220> FEATURE:
<223> OTHER INFORMATION: Artificial mouse PD-1 primer, sense strand

<400> SEQUENCE: 17
atctacctct gtggggccat                                               20

<210> SEQ ID NO 18
<211> LENGTH: 20
<212> TYPE: DNA
<213> ORGANISM: Artificial Sequence
<220> FEATURE:
<223> OTHER INFORMATION: Artificial mouse PD-1 primer, antisense strand

<400> SEQUENCE: 18
gagtgtcgtc cttgcttcca                                               20
```

```
<210> SEQ ID NO 19
<211> LENGTH: 20
<212> TYPE: DNA
<213> ORGANISM: Artificial Sequence
<220> FEATURE:
<223> OTHER INFORMATION: Artificial mouse CTLA-4 primer, sense strand

<400> SEQUENCE: 19
tactctgctc cctgaggacc                                              20

<210> SEQ ID NO 20
<211> LENGTH: 20
<212> TYPE: DNA
<213> ORGANISM: Artificial Sequence
<220> FEATURE:
<223> OTHER INFORMATION: Artificial mouse CTLA-4 primer, antisense
      strand

<400> SEQUENCE: 20
ccgtgtcaac agctctcagt                                              20

<210> SEQ ID NO 21
<211> LENGTH: 20
<212> TYPE: DNA
<213> ORGANISM: Artificial Sequence
<220> FEATURE:
<223> OTHER INFORMATION: Artificial mouse Cytochrome C primer, sense
      strand

<400> SEQUENCE: 21
cccccagcct cccttatctt                                              20

<210> SEQ ID NO 22
<211> LENGTH: 20
<212> TYPE: DNA
<213> ORGANISM: Artificial Sequence
<220> FEATURE:
<223> OTHER INFORMATION: Artificial mouse Cytochrome C primer, antisense
      strand

<400> SEQUENCE: 22
ggtctgccct ttctcccttc                                              20

<210> SEQ ID NO 23
<211> LENGTH: 20
<212> TYPE: DNA
<213> ORGANISM: Artificial Sequence
<220> FEATURE:
<223> OTHER INFORMATION: Artificial mouse Caspase 3 primer, sense strand

<400> SEQUENCE: 23
gagcttggaa cggtacgcta                                              20

<210> SEQ ID NO 24
<211> LENGTH: 20
<212> TYPE: DNA
<213> ORGANISM: Artificial Sequence
<220> FEATURE:
<223> OTHER INFORMATION: Artificial mouse Caspase 3 primer, antisense
      strand

<400> SEQUENCE: 24
ccgtaccaga gcgagatgac                                              20
```

```
<210> SEQ ID NO 25
<211> LENGTH: 21
<212> TYPE: DNA
<213> ORGANISM: Artificial Sequence
<220> FEATURE:
<223> OTHER INFORMATION: Artificial mouse Caspase 8 primer, sense strand

<400> SEQUENCE: 25
aacattcgga ggcatttctg t                                             21

<210> SEQ ID NO 26
<211> LENGTH: 21
<212> TYPE: DNA
<213> ORGANISM: Artificial Sequence
<220> FEATURE:
<223> OTHER INFORMATION: Artificial mouse Caspase 8 primer, antisense
      strand

<400> SEQUENCE: 26
agaagagctg taacctgtgg c                                             21

<210> SEQ ID NO 27
<211> LENGTH: 20
<212> TYPE: DNA
<213> ORGANISM: Artificial Sequence
<220> FEATURE:
<223> OTHER INFORMATION: Artificial mouse Caspase 7 primer, sense strand

<400> SEQUENCE: 27
tttccccaaa gctgccctcg                                               20

<210> SEQ ID NO 28
<211> LENGTH: 20
<212> TYPE: DNA
<213> ORGANISM: Artificial Sequence
<220> FEATURE:
<223> OTHER INFORMATION: Artificial mouse Caspase 7 primer, antisense
      strand

<400> SEQUENCE: 28
gcgtcaatgt cgttgatggg                                               20

<210> SEQ ID NO 29
<211> LENGTH: 20
<212> TYPE: DNA
<213> ORGANISM: Artificial Sequence
<220> FEATURE:
<223> OTHER INFORMATION: Artificial mouse Caspase 9 primer, sense strand

<400> SEQUENCE: 29
ctctgaagac ctgcagtccc                                               20

<210> SEQ ID NO 30
<211> LENGTH: 20
<212> TYPE: DNA
<213> ORGANISM: Artificial Sequence
<220> FEATURE:
<223> OTHER INFORMATION: Artificial mouse Caspase 9 primer, antisense
      strand

<400> SEQUENCE: 30
ctgctccaca ttgccctaca                                               20

<210> SEQ ID NO 31
<211> LENGTH: 20
<212> TYPE: DNA
<213> ORGANISM: Artificial Sequence
```

```
<220> FEATURE:
<223> OTHER INFORMATION: Artificial mouse P53 primer, sense strand

<400> SEQUENCE: 31
accagggcaa ctatggcttc                                              20

<210> SEQ ID NO 32
<211> LENGTH: 20
<212> TYPE: DNA
<213> ORGANISM: Artificial Sequence
<220> FEATURE:
<223> OTHER INFORMATION: Artificial mouse P53 primer, antisense strand

<400> SEQUENCE: 32
agtggatcct ggggattgtg                                              20

<210> SEQ ID NO 33
<211> LENGTH: 20
<212> TYPE: DNA
<213> ORGANISM: Artificial Sequence
<220> FEATURE:
<223> OTHER INFORMATION: Artificial mouse BAD primer, sense strand

<400> SEQUENCE: 33
cagcgtacgc acacctatcc                                              20

<210> SEQ ID NO 34
<211> LENGTH: 20
<212> TYPE: DNA
<213> ORGANISM: Artificial Sequence
<220> FEATURE:
<223> OTHER INFORMATION: Artificial mouse BAD primer, antisense strand

<400> SEQUENCE: 34
cgggatcgga cttcctcaag                                              20

<210> SEQ ID NO 35
<211> LENGTH: 20
<212> TYPE: DNA
<213> ORGANISM: Artificial Sequence
<220> FEATURE:
<223> OTHER INFORMATION: Artificial mouse BID primer, sense strand

<400> SEQUENCE: 35
tctgaggtca gcaacggttc                                              20

<210> SEQ ID NO 36
<211> LENGTH: 20
<212> TYPE: DNA
<213> ORGANISM: Artificial Sequence
<220> FEATURE:
<223> OTHER INFORMATION: Artificial mouse BID primer, antisense strand

<400> SEQUENCE: 36
tttgtcttcc tccgacaggc                                              20

<210> SEQ ID NO 37
<211> LENGTH: 20
<212> TYPE: DNA
<213> ORGANISM: Artificial Sequence
<220> FEATURE:
<223> OTHER INFORMATION: Artificial mouse BAX primer, sense strand

<400> SEQUENCE: 37
ctggatccaa gaccagggtg                                              20
```

<210> SEQ ID NO 38
<211> LENGTH: 20
<212> TYPE: DNA
<213> ORGANISM: Artificial Sequence
<220> FEATURE:
<223> OTHER INFORMATION: Artificial mouse BAX primer, antisense strand

<400> SEQUENCE: 38
cctttcccct tcccccattc                                              20

<210> SEQ ID NO 39
<211> LENGTH: 20
<212> TYPE: DNA
<213> ORGANISM: Artificial Sequence
<220> FEATURE:
<223> OTHER INFORMATION: Artificial mouse BCL2 primer, sense strand

<400> SEQUENCE: 39
agcatgcgac ctctgtttga                                              20

<210> SEQ ID NO 40
<211> LENGTH: 20
<212> TYPE: DNA
<213> ORGANISM: Artificial Sequence
<220> FEATURE:
<223> OTHER INFORMATION: Artificial mouse BCL2 primer, antisense strand

<400> SEQUENCE: 40
gccacacgtt tcttggcaat                                              20

<210> SEQ ID NO 41
<211> LENGTH: 20
<212> TYPE: DNA
<213> ORGANISM: Artificial Sequence
<220> FEATURE:
<223> OTHER INFORMATION: Artificial mouse BCL-XL primer, sense strand

<400> SEQUENCE: 41
ttgtacctgc ttgctggtcg                                              20

<210> SEQ ID NO 42
<211> LENGTH: 20
<212> TYPE: DNA
<213> ORGANISM: Artificial Sequence
<220> FEATURE:
<223> OTHER INFORMATION: Artificial mouse BCL-XL primer, antisense
     strand

<400> SEQUENCE: 42
cccggttgct ctgagacatt                                              20

<210> SEQ ID NO 43
<211> LENGTH: 15
<212> TYPE: DNA
<213> ORGANISM: Artificial Sequence
<220> FEATURE:
<223> OTHER INFORMATION: Artificial mouse BAK primer, sense strand

<400> SEQUENCE: 43
cctgggccaa cacgc                                                   15

<210> SEQ ID NO 44
<211> LENGTH: 21
<212> TYPE: DNA
<213> ORGANISM: Artificial Sequence
<220> FEATURE:
<223> OTHER INFORMATION: Artificial mouse BAK primer, antisense strand

```
<400> SEQUENCE: 44
ctgtgggctg aagctgttct a                                               21
```

COMPOSITIONS AND METHODS FOR TREATING CANCER

RELATED APPLICATIONS

This application is a National Stage of PCT/US2016/020864, filed Mar. 4, 2016, which claims the benefit of the filing date of U.S. Provisional Patent Application No. 62/131,343, filed Mar. 11, 2015, the contents of which applications are hereby incorporated by reference.

STATEMENT AS TO RIGHTS TO INVENTIONS MADE UNDER FEDERALLY SPONSORED RESEARCH AND DEVELOPMENT

This invention was made with Government support of Grant Nos. AT6681 and NS83054, awarded by the National Institutes of Health. The Federal Government has certain rights in this invention.

TECHNICAL FIELD

The present invention generally relates to methods for treating cancer. One aspect of the invention provides a method of treating a cancer including administrating an antibody against p40 monomer to a human or veterinary subject in need of such treatment.

BACKGROUND

Cancer is the deadliest disease that kills millions of people every year in this world. Understanding mechanisms by which cancer cells escape death and identifying the associated therapeutic target are important areas of research. Suppression of cell-mediated inflammation (1) is believed to be one of the major reasons for the persistence and progression of this fatal disease. However, mechanisms by which this high level of suppression is maintained and tumor cells escape death are poorly understood. Since IL-12 is the most important cytokine in terms of cell-mediated immunity (2), this molecule is always under scanner for the treatment of cancer (3, 4). IL-12 family of cytokines has four different members including p40 monomer (p40), p40 homodimer ($p40_2$), IL-12 (p40:p35), and IL-23 (p40:p19). In this era of science, where heterodimers rule, only IL-23 and IL-12 were thought to have biological functions. As a result, p40 and p402 were considered as nonfunctional members of the IL-12 family (5). However, we have demonstrated the proinflammatory property of $p40_2$ (6-8) and delineated that biological functions of p402 are different from that of IL-12 and IL-23 (9, 10). Furthermore, after raising separate functional blocking monoclonal antibodies (mAb) and ELISA against each of mouse $p40_2$ and p40 (11), we have delineated that mAb against $p40_2$ protects mice against EAE (12).

Here, we demonstrate that different forms of cancer cells except the lung cancer one are associated with specific elevation of p40. Selective ablation of p40 by mAb stimulates cell death in different cancer cells and in vivo in TRAMP tumor tissue. Furthermore, p40 suppresed the caveolin-mediated internalization of IL-12Rβ1 and associated IL-12 signaling that were neutralized by p40 mAb. These results delineate a novel pathogenic role of p40, in which it helps cancer cells to evade cell death.

SUMMARY OF THE PREFERRED EMBODIMENTS

In one aspect, the present invention provides a method for treating a cancer including administering to a subject in need of such treatment a composition comprising a therapeutically effective amount of an antibody against p40 monomer or an immunologically active fragment thereof. In one embodiment, the antibody or immunologically active fragment suppresses inhibition of IL-12 signaling. In another embodiment, the antibody or immunologically active fragment upregulates production of IFN-γ. In another embodiment, the antibody or immunologically active fragment thereof at least reduces the internalization of IL-12Rβ1 via a caveolin-mediated pathway.

The antibody or immunologically active fragment thereof may be a monoclonal antibody or an immunologically active fragment of a monoclonal antibody. In other embodiments, the antibody or immunologically active fragment thereof is a polyclonal, monoclonal, human, humanized, and chimeric antibody; a single chain antibody or an epitope-binding antibody fragment of such an antibody. The antibody or immunologically active fragment may not significantly neutralize the biological action of p40 homodimer. In another embodiment, the antibody or immunologically active fragment thereof is a humanized antibody or an immunologically active fragment thereof.

The cancer may be, for example, prostate cancer, breast cancer or liver cancer. In another embodiment, the cancer is characterized by excess production of p40 monomer.

In one embodiment, the composition also includes at least one pharmaceutically acceptable carrier. The composition may be administered orally. In other embodiments, the composition is administered by a subcutaneous, intra-articular, intradermal, intravenous, intraperitoneal or intramuscular route. In yet other embodiments, the subject is a human subject.

Another aspect provides a method for inducing cell death in a cell including contacting the cell with an amount of an antibody against p40 monomer or an immunologically active fragment thereof, where the amount is an amount sufficient to induce the death of the cell. In one embodiment, the cell is a cancer cell. The cancer cell may be a cancer cell exhibiting excess production of p40 monomer. In other embodiments, the cancer cell is a prostate cancer cell, a breast cancer cell or a liver cancer cell.

BRIEF DESCRIPTION OF THE DRAWINGS

FIG. 13: Effect of p40, p40$_2$, p70, p40 mAb, and IgG on the surface expression IL-12Rβ2 in cultured TRAMP cells. (A) FACS analyses to monitor the level of IL-12Rβ2 in cultured TRAMP cells treated with p40 (20 ng/mL), p40$_2$ (20 ng/mL), p70 (20 ng/mL), p40 mAb (0.5 µg/mL), and mouse IgG (0.5 µg/mL) for 2 hrs under serum-free condition. Results represent three different experiments.

DETAILED DESCRIPTION OF THE PREFERRED EMBODIMENTS

Definitions

Figure 1A:
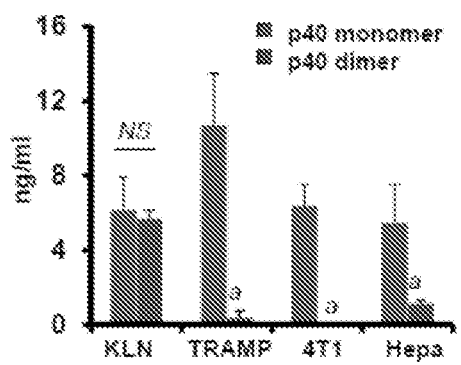
FIG. 1: Levels of IL-12 family of cytokines in different cancer cells. Levels of p40 (left bar) and $p40_2$ (right bar) (A), IL-12 (B) and IL-23 (C) were measured in supernatants of cultured mouse squamous (KLN), prostate (TRAMP), breast (4T1), and liver hepatoma1-6 (Hepa) tumor cells by sandwich-ELISA. Results are mean±SD of three different experiments. $^a p<0.001$ vs. p40 measured in respective tumor cells. (D) TRAMP supernatants from three separate experiments were passed through 10 kDa cut column followed by native PAGE analysis and Coomassie blue staining. The p40 band was detected by comparing with pure p40 protein (extreme left column). (E) Native PAGE immunoblot analyses of p40 in the supernatants of TRAMP from three separate experiments. (F) Intracellular FACS assay of p40 and $p40_2$ in cultured TRAMP cells. (E) Mean fluorescence intensity analyses were plotted to represent levels of intracellular p40 and $p40_2$ in TRAMP cells from three independent experiments. *$p<0.01$ vs. p40; NS, not significant. Native protein gel analyses followed by coomassie staining were performed to detect the level of p40 in the concentrated supernatants of human hepatoma Hep3B (H), prostate LnCAP (I), and breast cancer cell line MCF-7 (J). Native PAGE immunoblot analyses of p40 and other IL-12 members of cytokines (K) in the concentrated supernatants of different cancer cells.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a drug means an amount of the drug which imparts a therapeutic effect to the human or veterinary patient.

The term "internalization" as used herein means a process in which molecules, such as proteins, are engulfed by the cell membrane and drawn into the cell.

The term "antibody" herein is used in the broadest sense and specifically covers, for example, monoclonal antibodies, polyclonal antibodies, multispecific antibodies and antibody fragments etc., so long as these fragments exhibit the desired immunological activity.

Methods for Treating a Cancer

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

One aspect of the invention provides a method of treating a cancer, for example prostate cancer. Prostate cancer is the most common form of male cancer that develops in the prostate in elderly people. Since the impairment of immune system is also very common among elderly population, several immunotherapies including activation of tumor-specific T cells, inflammatory cytokine production, and the activation of antigen-presenting cells are possible approaches to fight against this deadly disease (19).

However, the present method is not limited to the treatment of prostate cancer. The method is applicable to the treatment of many other cancers including, but not limited to, lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. In preferred embodiments, the method is applicable to cancers characterized by an overproduction of p40 monomer.

IL-12 is the most important cytokine that triggers cell-mediated immune response. IL-12 consists of a heavy chain (p40) and a light chain (p35) linked covalently by disulfide bonds to give rise to the so-called bioactive heterodimeric (p70) molecule (5). It is produced mainly by antigen presenting cells upon activation through Toll-like receptors and by interactions with CD4+ T cells (5, 20). Eventually, p40 has been shown to pair with p19 to form a newly discovered cytokine, IL-23 (21). Either p19 or p35 is constitutively expressed in many cell types. It is known that dendritic cells and macrophages, cells which are able to secrete heterodimeric IL-12 or IL-23, always produce an excess of p40 as monomer (p40) or homodimer (p40$_2$) (5). However, the biological functions of p40$_2$ and p40 have remained unknown The results presented herein demonstrate that, in many different cancers, cancer cells produce excess p40 as compared to $p40_2$, IL-12 and IL-23 and that p40 is involved in cancer cell survival. This conclusion is based, in part, on the following observations: First, the level of p40 was much higher in TRAMP, 4T1 and Hepa cells as compared to $p40_2$, IL-12 and IL-23. This selective increase in p40 was not observed in this specific KLN lung cancer cell line, indicating the specificity of this finding. However, this lack of a selective increase in p40 may not be a general feature of lung cancer. Second, neutralization of p40, but not $p40_2$, induced the release of LDH in TRAMP, 4T1, and Hepa cells. Alternatively, mAb against p40, but not $p40_2$, reduced MTT metabolism in TRAMP, 4T1 and Hepa cells. Again, p40 mAb had no effect on LDH and MTT in KLN cells. Third, t-type calcium influx, a growth supportive event in cancer cells, was significantly reduced in TRAMP, 4T1 and Hepa, but not KLN, cells when treated with p40 neutralizing antibody. Fourth, TUNEL and Annexin-V staining experiments displayed more death in TRAMP, 4T1 and Hepa, but not KLN, cells after treatment with p40 mAb. Finally, intraperitoneal injection of p40 mAb, but not IgG, significantly reduced the size of the prostate tumors grown in the flank of male C57BL/6 mice. This is an unexpected result, demonstrating a biological role of p40 monomer, the so-called non-functional member of the IL-12 family, in cancer cell survival. Furthermore, these results indicate the possible therapeutic prospect of the p40 neutralization in various cancers.

While investigating mechanisms behind p40-mediated killing of tumor cells, the inventors observed upregulation of IFNγ, a major cytotoxic inflammatory cytokine (22-24), by p40 mAb in pure TRAMP cells. This observation is striking as T lymphocytes (25) and natural killer cells (26) are considered as primary sources of IFN-γ. However, previous literatures demonstrate that it can be produced by murine macrophages (27) as well as epithelial cells (28, 29), prompting the inventors to examine IFN-γ production in TRAMP epithelial cells. TRAMP cells expressed very low amount of IFNγ in unstimulated condition and p40 mAb treatment stimulated the production of IFNγ by several fold. Moreover, cancer cells with epithelial origin such as 4T1 and hepatocellular origin such as Hepa also expressed significant amount of IFNγ when treated with p40 mAb further suggesting that functional blocking of p40 could stimulate IFNγ production in a wide range of cancer cells. Consistent with the cytotoxic nature of IFNγ, neutralization of this molecule abrogated p40 mAb-mediated death of TRAMP, 4T1 and Hepa cells, demonstrating that p40 mAb induces death of cancer cells via IFNγ.

Activation of the IL-12 signaling pathway plays a critical role in the induction of IFNγ in various cells (5). Interaction of IL-12 and its receptor IL-12R in the plasma membrane triggers the activation of Janus family of tyrosine kinases that in turn phosphorylates the tyrosine residues of signal transducer and activator of transcription 3 and 4 (STAT3 and STAT4). These tyrosine phosphorylations are responsible for the formation of STAT4/STAT4 homodimer and STAT3/STAT4 heterodimers. These dimers then translocate to the nucleus and bind to IFNγ promoter for the transcription of IFNγ (30).

Accordingly, p40 mAb stimulated the production of IL-12 in TRAMP cells, suggesting that the absence of p40 may favor the interaction of IL-12 with IL-12R to turn on the positive autoregulatory effect of IL-12 (31) in these cells. A successful interaction between IL-12 and IL-12R transmits the downstream signal and then internalizes the receptor inside the cell. On the other hand, an unsuccessful interaction between IL-12 and IL-12R leaves the receptor arrested in the membrane, which is unable to transmit any downstream signaling cascade. p40 treatment increased the membrane localization of IL-12Rβ1 and p40 mAb decreased the level of IL-12Rβ1 in the membrane. On the other hand, either p40 or p40 mAb did not have any effect on the internalization of IL-12Rβ2. These results demonstrate that p40 is involved in the membrane arrest of IL-12Rβ1, but not IL-12Rβ2. To further explore the mechanism, the inventors examined whether p40 mAb-mediated internalization of IL-12Rβ1 in TRAMP cells was dependent on clathrin or caveolin. In this case, caveolin, but not clathrin, was found to be involved in p40 mAb mediated membrane internalization of IL-12Rβ1.

It has been reported that $p40_2$ is an antagonist of IL-12 as the former competes with the latter for binding to IL-12Rβ1 (5). On the other hand, p40 reportedly does not have any IL-12-antagonizing activity and binds IL-12Rβ1 very weakly (10 to 20 times less potent compared to p402) (5). In contrast to these reports, the results presented herein from TRAMP cells suggest that it is p40 monomer, but not $p40_2$, that antagonizes IL-12 signaling via suppressing caveolin-mediated internalization of IL-12Rβ1. Therefore, this is a paradigm shift of knowledge. Since neutralization of p40 by p40 mAb reinstalls the internalization of IL-12Rβ1 and induces death via IL-12-mediated production of IFN-γ, p40 mAb may have therapeutic efficacy in prostate and other cancers, which are associated with excessive production of p40.

In one aspect, the invention provides a method of treating a cancer human or veterinary subject including administering a therapeutically effective amount of a composition including at least one antibody directed against p40 or an immunoreactive fragment of such an antibody. In various embodiments, the antibody is, for example, a polyclonal antibody, a monoclonal antibody, a humanized antibody, a human antibody, a chimeric antibody, a Fab fragment, a Fab' fragment, a F(ab)2 fragment, or a single chain Fv (scFv) fragment. In other embodiments, the antibody or antibody fragment is linked to another molecule to form an immunoconjugate molecule. For example, the antibody or antibody fragment may be linked to a cytotoxic agent, possibly through a linker. The antibody or antibody fragment encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Pharmaceutical Compositions

Another aspect of the present invention provides pharmaceutical compositions including at least one antibody or antibody fragment to p40 monomer. For example, the pharmaceutical composition may include 1, 2, 3, 4, 5 or more of such antibodies. The antibody or antibody fragment can be, but need not be, administered in combination with another therapeutic substance. For example, it may be combined with a cytotoxic drug or other anti-cancer agent.

The pharmaceutical compositions can be in the form of, for example, tablets, pills, dragees, hard and soft gel capsules, granules, pellets, aqueous, lipid, oily or other solutions, emulsions such as oil-in-water emulsions, liposomes, aqueous or oily suspensions, syrups, alixiers, solid emulsions, solid dispersions or dispersible powders. In pharmaceutical compositions for oral administration, the agent may be admixed with commonly known and used adjuvants and excipients, for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration the agent or pharmaceutical compositions of the agent can be in the form of an aqueous, lipid, oily or other kind of solution or suspension or even administered in the form of liposomes or nano-suspensions.

Modes of Administration

The p40 monomer antibody or antibody fragment or pharmaceutical compositions including the antibody or fragment thereof can be administered by any method that allows for the delivery of a therapeutic effective amount of the agent to the subject. Modes of administration can include, but are not limited to oral, topical, transdermal and parenteral routes, as well as direct injection into a tissue and delivery by a catheter. Parenteral routes can include, but are not limited to subcutaneous, intradermal, intra-articular, intravenous, intraperitoneal and intramuscular routes. In one embodiment, the route of administration is by topical or transdermal administration, such as by a lotion, cream, a patch, an injection, an implanted device, a graft or other controlled release carrier. Routes of administration include any route which directly delivers the composition to the systemic circulation (e.g., by injection), including any parenteral route. Alternatively, administration can be by delivery directly to the affected tissue.

One embodiment of the method of the invention comprises administering at least one p40 monomer antibody or a fragment thereof, in a dose, concentration and for a time sufficient to prevent the development of, or to lessen the extent of a cancer, for example, any of the cancers mentioned above. Certain embodiments include administering systemically the p40 monomer antibody or a fragment thereof in a dose between about 0.1 micrograms and about 100 milligrams per kilogram body weight of the subject, between about 0.1 micrograms and about 10 milligrams per kilogram body weight of the subject, between about 0.1 micrograms and about 1 milligram per kilogram body weight of the subject. In practicing this method, the p40 monomer antibody or therapeutic composition containing the agent can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

Embodiments of the invention will be further described in the following examples, which do not limit the scope of the invention described in the claims.

Example 1—Materials and Methods

Animals and Regents: All murine cancer cell lines were purchased from ATCC. Male C57 BL/6 mice (Harlan) were used for this study. Mouse p40 (cat #554594) and p70 (cat #554592) were purchased from BD Biosciences. Mouse $p40_2$ (cat #499-ML) was purchased from R&D. Hamster IgG (cat #IR-HT-GF) was obtained from Innovative Research. Mouse IgG (cat #sc-2025) was purchased from Santa Cruz Biotechnology. Chloropromazine (cat #C8138), filipin (cat #F9765), MTT assay kit (cat #CGD1), and LDH assay kit (cat #TOX7) were purchased from Sigma. IFNγ neutralizing antibody (cat #16-7311-81) was purchased from eBioscience. TUNEL assay kit (cat #QIA39) was purchased from Calbiochem and Annexin V assay kit (cat #K101-25) was purchased from Biovision.

Sandwich ELISA: Sandwich ELISA was used to quantify mouse $p40_2$ and p40 as described by us (11, 12). Briefly, for $p40_2$, mAb a3-1d (1.3 mg/mL) was diluted 1:3000 and added to each well (100 μL/well) of a 96-well ELISA plate for coating. The biotinylated $p40_2$ mAb d7-12c (2 mg/mL) was diluted 1:3000 and used as detection antibody. Similarly for p40, mAb a3-3a (1.3 mg/mL) and biotinylated p40 mAb a3-7 g (2 mg/mL) were also diluted 1:3000 and used as coating and detection antibodies, respectively (11). Concentrations of IFN-γ, IL-12 and IL-10 were measured in serum free supernatants of different treatment groups by ELISA (eBioscience), according to the manufacturer's instructions.

MTT and LDH assays: These assays were performed as described by Jana. M. et al. (32) and Khasnavis. S. et al. (33).

Tumor development and measurement: Animal maintaining and experiments were in accordance with National Institute of Health guidelines and were approved by the Institutional Animal Care and Use committee (IACUC #14-019) of the Rush University of Medical Center, Chicago, Ill. Tumors were generated subcutaneously in male C57 BL/6 mice. Mice were injected with 1×106 TRAMP-C2 cells in their flank for tumor generation. Mice were maintained in our temperature-controlled animal vivarium with adequate food and water. Tumor growth was measured with a caliper and tumor cross-sectional area was determined with the formula (mm2=longest diameter X shortest diameter). Treatment with p40 mAb started when the tumor sizes reached 0.8-1 cm2. The p40 mAb a3-3a was injected once a week intraperitonially in 0.1 ml volume of sterile PBS-1% normal mouse serum. The tumors were then measured to determine regression or progression. Infrared dye (Alexa 800-conjugated 2DG dye; Licor) was injected via tail-vein on the day before imaging analysis. Mice were sacrificed at the end of the study and tumor tissues were collected appropriately for western blot, mRNA expression and immunohistochemical analysis.

Tissue preparation and Immunohistochemistry: Paraffin embedded tissue sections were prepared and tissue sections were cut 5 micron in size. To eliminate endogenous peroxidase activity, tissue sections were deparaffinized, rehydrated and incubated with 3% H2O2 in methanol for 15 min at room temperature. Antigen retrieval was performed at 95° C. for 20 min by placing the slides in 0.01 M sodium citrate buffer (pH 6.0). After blocking, the slides were then incubated with the primary antibodies (Table 1) at 2 h room temperature followed by washing and incubation with Cy2, Cy3 or Cy5 (Jackson ImmunoResearch Laboratories, West Grove, Pa.) secondary antibodies at RT for 1 h. Mouse IgG was used as an isotype control (34).

TUNEL assay: Following treatments with mAb against either p40 or $p40_2$, TUNEL assays were performed as described by Corbett G T et al. (35).

Semi-quantitative RT-PCR: Total RNA was isolated and semi-quantitative RT-PCR analyses for IFNγ, IL-10, T-bet, GATA3, FoxP3, and GAPDH were performed as described by Brahmachari S et al. (6); Jana M et al. (32) and Corbett G T et al. (35) using primers (Table 2).

Real-time quantitative PCR: The mRNA quantification was performed using the ABI-Prism7700 sequence detection system (Applied Biosystems) using SYBR GREEN (Applied Biosystems) as described by Brahmachari S et al. (6); Jana M et al. (32) and Corbett G T et al. (35). The mRNA expressions of respective genes were normalized to the level of GAPDH mRNA. Data were processed by the ABI Sequence Detection System 1.6 software and analyzed by ANOVA.

FACS: Surface expression of IL-12Rβ1 and IL-12Rβ2 were monitored as described by Brahmachari S et al. (6). Briefly, after treatment, cells were incubated for 10 min with Accutase (BD Bioscience) for detachment of adherent cells. After washing with FACS buffer, cells were incubated with PEtagged IL-12Rβ1 and IL-12Rβ2 antibodies at 4° C. for 1 h. For intracellular staining, permeabilization was done before incubation with p40 and $p40_2$ mAbs. APC-conjugated antihamster secondary antibodies were used. After washing, the cells were analyzed through FACS (BD Biosciences, San Jose, Calif.). Cells were gated based on morphological characteristics. Apoptotic and necrotic cells were not accepted for FACS analysis.

Membrane isolation: After treatment, cells were scraped in PBS and cell pellets were dissolved in homogenization buffer (250 mM sucrose, 1 mM EDTA, 10 mM Tris-HCl, pH 7.2, protease inhibitors and phosphatase inhibitors) and then homogenized with hand homogenizer. Cell debris was removed by centrifugation at 500 g for 10 min at 4° C. followed by centrifugation of supernatant at 100,000 g for 1 h. Supernatants were discarded and the pellet containing membrane fractions were dissolved in SDS-PAGE sample buffer.

Immunoblot analyses: Immunoblot analyses were performed as described by Jana M et al. (32) Khasnavis S (33) and Corbett G T et al. (35) using different primary antibodies (Table 1).

Statistical Analysis: For tumor regression, quantitative data were presented as the mean±SEM. Statistical significances were accessed via one-way ANOVA with Student-Newman-Keuls posthoc analysis. Other data were expressed as means±SD of three independent experiments. Statistical differences between means were calculated by the Student's t-test. A p-value of less than 0.05 ($p<0.05$) was considered statistically significant.

Figure 1B:
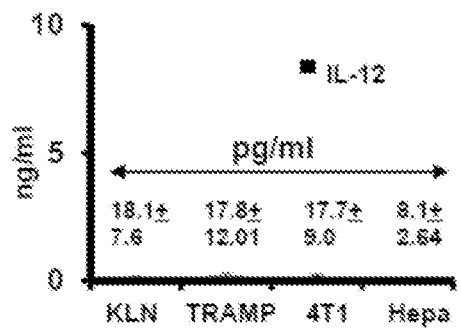
Figure 1C:
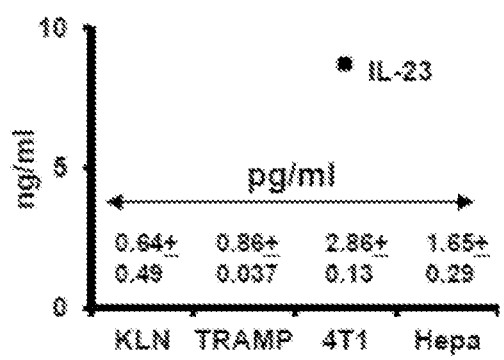
Figure 1D:
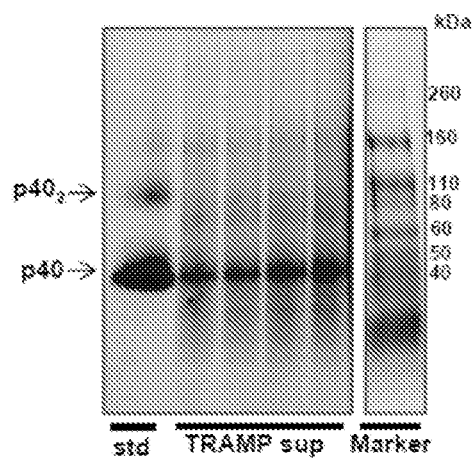
Figure 1E:
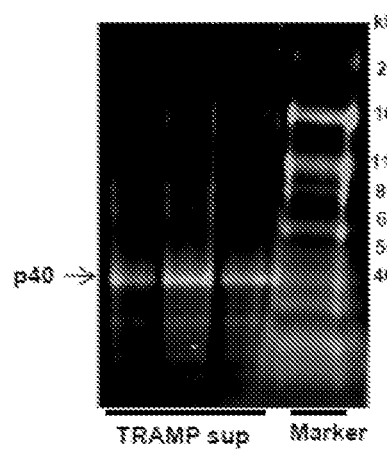
Figure 1F:
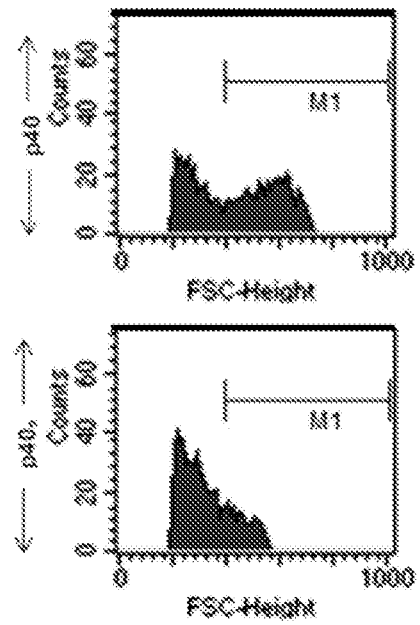
Figure 1G:
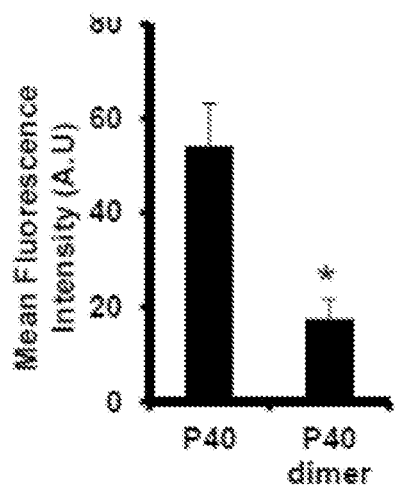

Example 2—Levels of IL-12 Family of Cytokines (p40, p402, IL-12, and IL-23) in Different Mouse Cancer Cell Lines To understand the role of IL-12 family of cytokines in cancer, at first, we monitored the level of these cytokines in different cancer cell lines. It was not possible to examine the role of p40 and $p40_2$ in the pathogenesis of any disease due to the unavailability of specific functional blocking monoclonal antibodies (mAb). Therefore, we have generated neutralizing mAbs against each of p40 and $p40_2$ and developed ELISA to monitor these cytokines separately (11). The quantification analyses were performed in different adherent mouse cancer cells including squamous (KLN), prostate (TRAMP), breast (4T1), and liver hepatoma (Hepa) cell lines. Cells were cultured under serum free condition for 48 hrs followed by measuring the levels of p40, $p40_2$, IL-12, and IL-23 by sandwich ELISA. In general, the levels of IL-12 and IL-23 were very low as compared to p40 and $p40_2$ in each of these cell lines (FIG. 1A-C). The level of p40 was much higher than $p40_2$, IL-12 or IL-23 in TRAMP, 4T1 and Hepa cells (FIG. 1A-C). However, levels of p40 and $p40_2$ were almost same in KLN lung cancer cells (FIG. 1A), suggesting the specificity of the effect. To confirm the presence of p40 in cancer cells, we adopted different techniques. First, we monitored the level of p40 in the supernatants of TRAMP cells by native PAGE analysis (FIG. 1D). Coomassie staining of native PAGE and comparing the band with pure monomeric p40 protein (extreme left lane) clearly indicates the presence of a 40 kDa protein as the major secretory molecule in TRAMP cells (FIG. 1D). Second, we performed native immunoblot analysis of supernatants of TRAMP cells with our specific p40 monomer monoclonal antibody (p40 mAb) a3-3a and found the presence of p40 in supernatants of TRAMP cells (FIG. 1E). Finally, intracellular FACS analyses with p40 mAb a3-3a and $p40_2$ mAb a3-1d show that the level of p40 was significantly higher than $p40_2$ in TRAMP cells (FIGS. 1F-G).

Figure 1H:
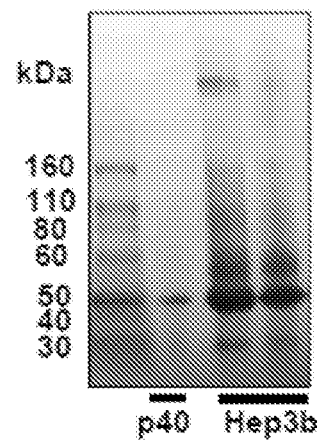
Figure 1I:
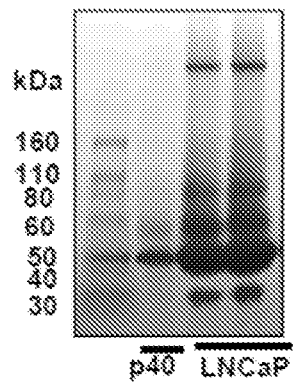
Figure 1J:
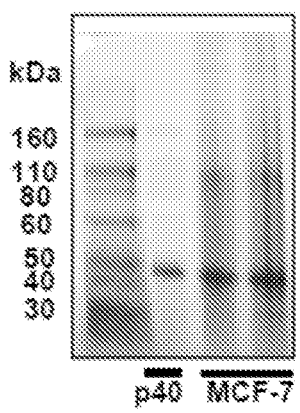
Figure 1K:
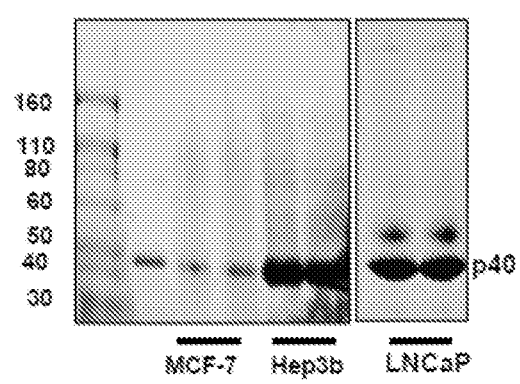
Figure 14A:
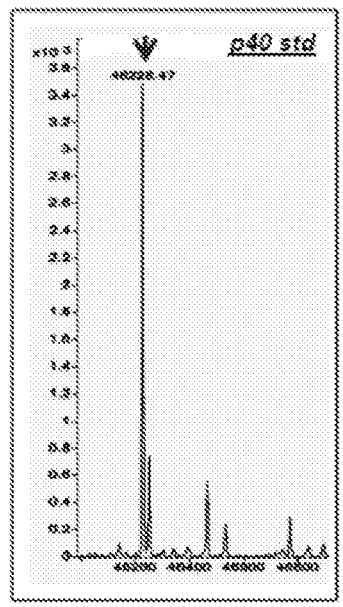
FIG. 14: Expression of p40 in different human cancer cell lines. ESI-MS analyses of p40 in the standard protein (A) human hepatoma Hep3b (B) and human prostate LnCAP (C) cell lines. Briefly, supernatants of different cancer cell lines were concentrated after passing through 10 kDa molecular cut column and then analyzed for p40 by ESI-MS technology. Similarly, the level of IL12 was analyzed in IL12 standard (D) Hep3B (E) and LnCAP (F) cell lines.
Figure 14B:
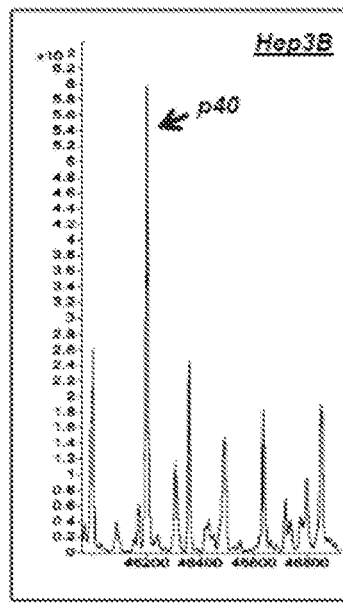
Figure 14C:
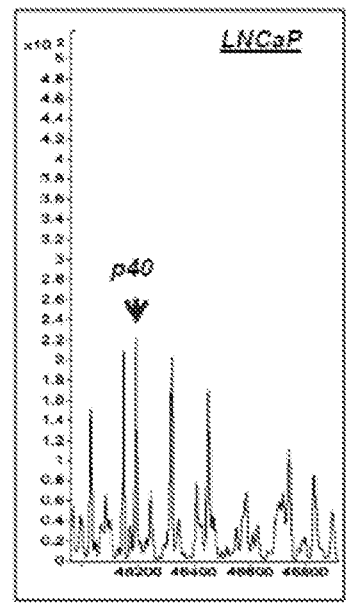
Figure 14D:
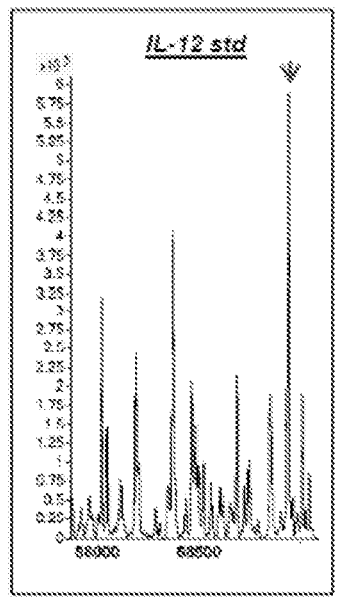
Figure 14E:
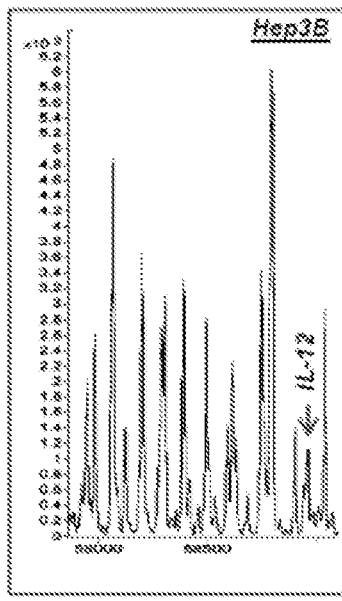
Figure 14F:
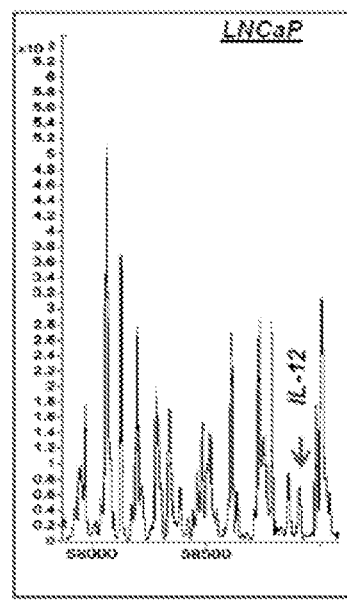

Next, we measured the level of p40 in different human cancer cell lines. Interestingly, our ESI-MS analyses (FIGS. 14A-C) in the supernatants clearly indicated that both human hepatoma Hep3B and prostate LNCaP cells expressed significantly higher level of p40 than IL12 (FIGS. 14D-F). Furthermore, native PAGE analyses followed by coomassie staining of supernatants along with p40 standard protein demonstrated that Hep3B, LNCaP and human breast MCF-7 cancer cells produced significant level of p40 (FIGS. 1H-J). Immunoblot analyses of different supernatants with anti-human pan IL12p40/p70 antibody also showed that all three human cancer cells produced a higher level of p40 compared to other IL-12 cytokines (FIG. 1K). Together, our results suggest that p40 is produced in excess by a wide spectrum of cancer cells.

Figure 2A:
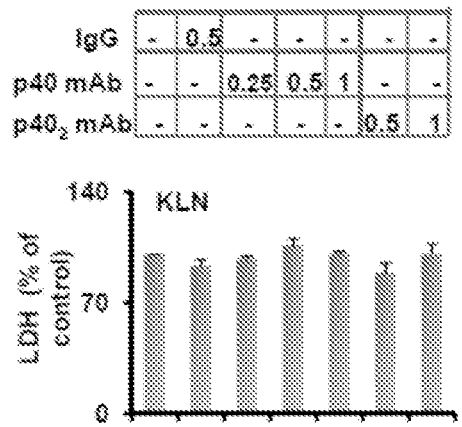
FIG. 2: Effect of monoclonal antibody-mediated specific neutralization of p40 and p40$_2$ on the death of cancer cells. KLN (A & E), TRAMP (B & F), 4T1 (C & G), and Hepa (D & H) cells were treated with neutralizing mAbs against p40 and p40$_2$ for 48 hrs under serum-free condition followed by monitoring cell death by LDH release (A-D) and MTT (E-H). *$p<0.01$ vs. control. T-type calcium influx was performed in KLN (I), TRAMP (J), 4T1 (K), and Hepa (L) cells, respectively. T-type calcium influx was measured in the presence of 1M KCl. TUNEL assay (M) and Phycoerithrin (PE)-tagged Annexin V staining (N) were performed in KLN, TRAMP, 4T1, and Hepa cells to monitor cell death. TUNEL-positive (O) and PE-annexinVpositive (P) cells were counted in 10 different images per group and then plotted as percent of control. All results are mean±SD of three different experiments. *$p<0.001$ vs respective controls for both TUNEL and AnnexinV assay. For FIGS. O and P: Control—left bar; IgG—left center bar; p40 mAb—right center bar; p402 mAb—right bar.
Figure 2B:
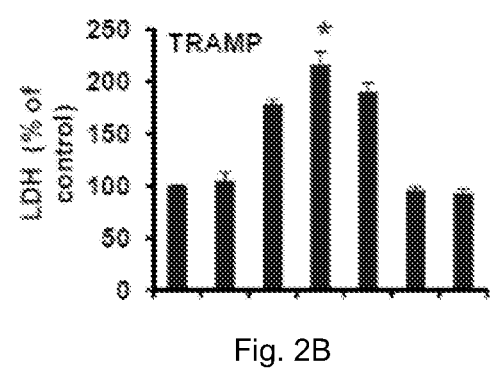
Figure 2C:
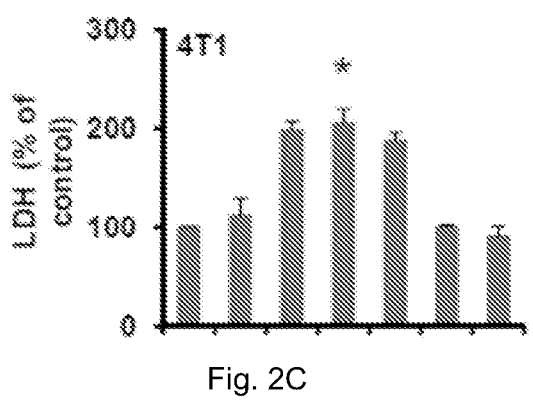
Figure 2D:
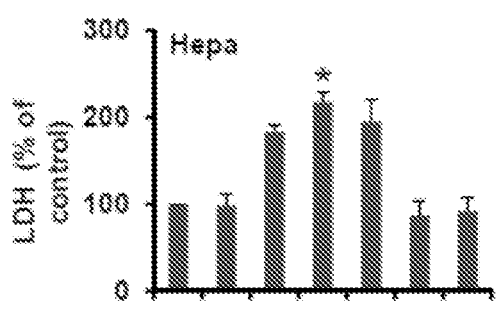
Figure 2K:
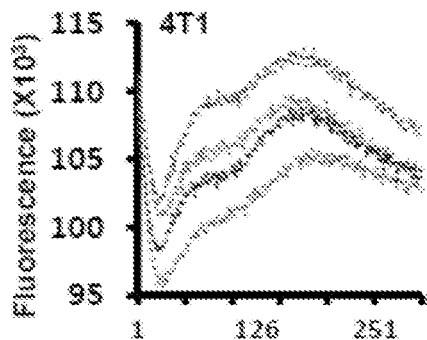
Figure 2L:
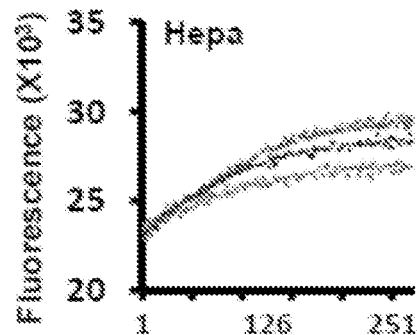
Figure 2M:
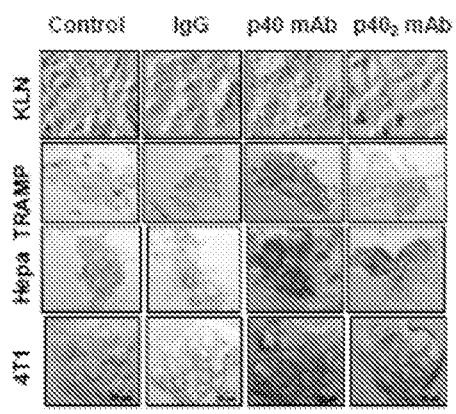
Figure 2N:
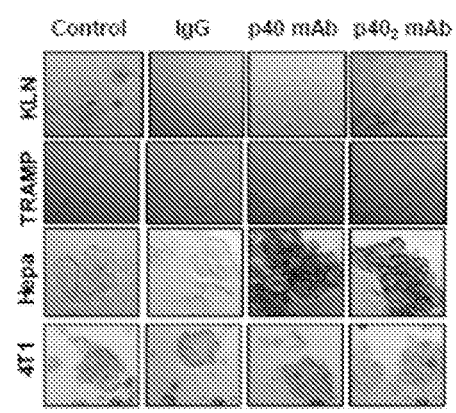
Figure 2O:
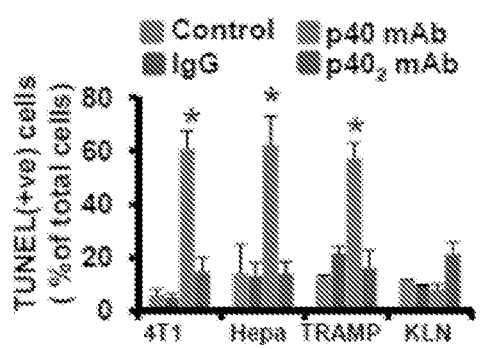
Figure 2P:
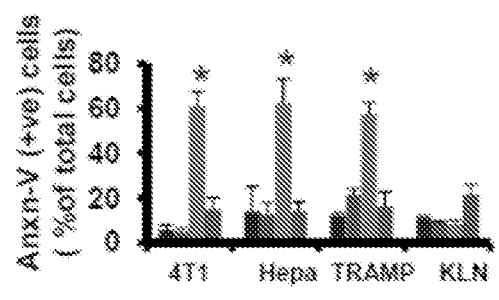

Example 3: Selective Neutralization of p40 by Monoclonal Antibody Stimulates the Death Response in Cancer Cells Since among the IL-12 family members, the level of p40 was the highest in most of the cancer cells, we examined its role in growth and survival of cancer cells. It is often quite straightforward to consider a knock out mouse model to investigate the role of a molecule in any disease process. However, we cannot use p40 (−/−) mice in this case because knocking out the p40 gene will knock down IL-12, IL-23, $p40_2$, and p40. Therefore, to investigate the role of $p40_2$ and p40 in life and death of different cancer cells, the only feasible approach is to use neutralizing monoclonal antibodies against these molecules. The p40 mAb a3-3a, but not $p40_2$ mAb a3-1d, increased release of LDH FIG. 2 (A-D) and decreased MTT FIG. 2 (E-H) in TRAMP FIG. 2 (B & F), 4T1 FIG. 2 (C & G) and Hepa FIG. 2 (D & H) cells. On the other hand, p40 mAb had not effect on either LDH or MTT in KLN lung cancer cells, indicating the specificity of the effect. To monitor death in tumor cells from another angle, we measured calcium influx through t-type calcium channel. Treatment of different cancer cells with p40, but not $p40_2$, mAb displayed a reduced t-type calcium influx in TRAMP (FIG. 2F), 4T1 (FIG. 2G) and Hepa (FIG. 4H) cells. Again, p40 mAb remained unable to modulate t-type calcium influx in KLN cancer cells (FIG. 2E). Accordingly, TUNEL (FIG. 2M) and Annexin V-labeling (FIG. 2N) followed by the quantitative analyses (FIGS. 2O & 2P) reiterated that neutralization of p40, but not $p40_2$, stimulated death in TRAMP, 4T1 and Hepa cancer cells. However, p40 mAb had no effect on the apoptosis of KLN cancer cells.

Together, these results suggest that specific ablation of p40, but not p40$_2$, stimulates the death response in prostate, breast and liver tumor cells, without altering the survival of lung cancer cells.

Figure 3A:
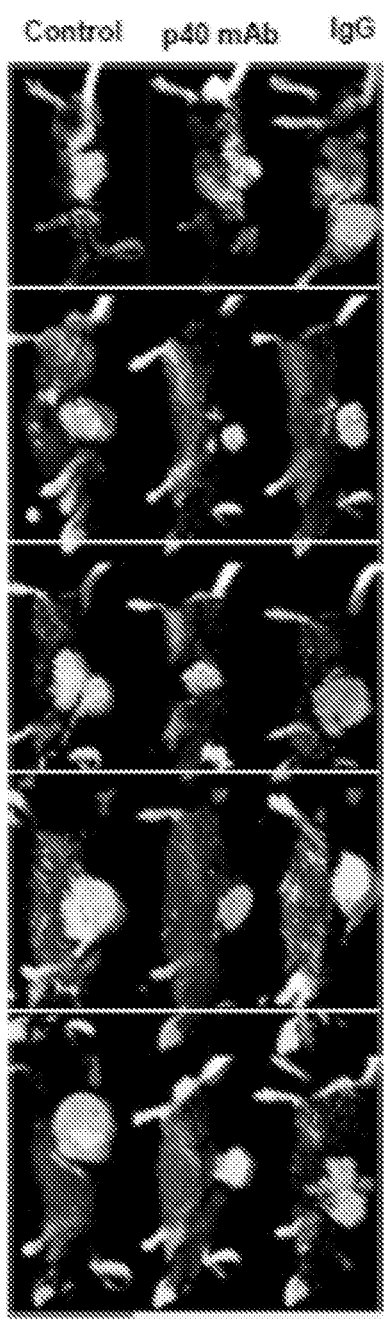
FIG. 3: Effect of p40 neutralizing antibody in the regression of TRAMP tumor in vivo in mice. (A) Eight to ten wks old male C57BL/6 (n=5 per group) were injected with 1 million of TRAMP cell suspension subcutaneously. After about 6 weeks, when tumors were within 0.8 to 1 mm in size, mice were treated with p40 mAb (middle panel) and hamster IgG (right panel) at a dose of 2 mg/kg body wt twice a week. After 2 wks, tumors were labeled with Alexa800 conjugated 2DG dye via tail vein injection and then imaged in Licor Odyssey infrared scanning machine. Results were compared with no treatment control group (Left panel). (B) Tumors were excised from the flank of all groups of mice. Five mice (n=5) were included in each group. (C) Tumor size was monitored every alternate day for all groups of mice and plotted in a comparative line plot. Results are mean±SEM of five different mice. (D) TUNEL assay in control, IgG, and p40 mAb-treated tumors (Green, β-actin; Red, TUNEL). (E) Custom mRNA array for 12 different apoptotic genes in control and p40 mAb-treated group, which was then plotted with heat map explorer software. (F) Real-time mRNA analyses of 12 apoptotic genes in three different groups. Results are mean±SEM of five mice per group. *$p<0.05$ vs. control and **$p<0.01$ vs. control group. Control—left bar; p40 mAb—center bar; IgG—right bar.
Figure 3B:
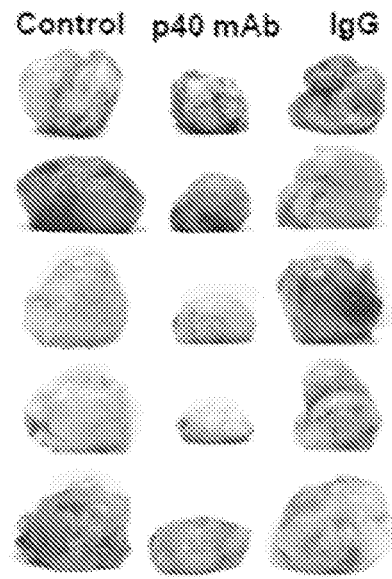

Specific neutralization of p40 induces the regression of tumor growth and stimulates the death response in vivo in TRAMP tumor tissues. Next, we examined the effect of p40 mAb on tumor size and the death of tumor tissue in vivo when TRAMP cells were grown as a tumor in the flank of male C57BL/6 mice. Once tumor reached 0.8 to 1 mm size, mice were treated with p40 mAa3-3a at a dose of 2 mg/Kg body weight via intraperitoneally twice a week for 2 weeks. The tumor size was recorded every alternate day after treatment of p40 mAb. Animals that received IgG were analyzed as negative controls. Control animals did not receive any antibody. After two weeks, tumors were labeled with infrared dye 800 conjugated 2 deoxy D glucose (IRDye800 2DG) via tail vein injection and then imaged in Licor Odyssey infrared scanner. Interestingly, we observed that administration of p40 mAb significantly reduced the size of tumors as evident from whole animal infrared images (FIG. 3A) and pictures of excised tumors (FIG. 3B).

Figure 3C:
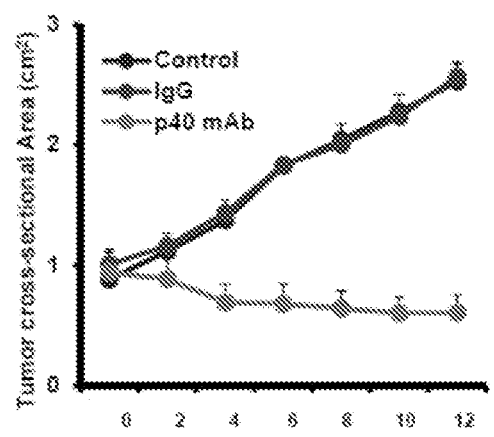
Figure 3D:
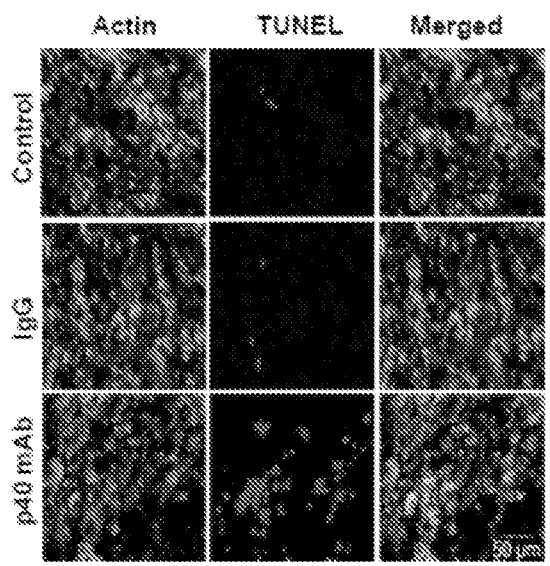
Figure 3E:
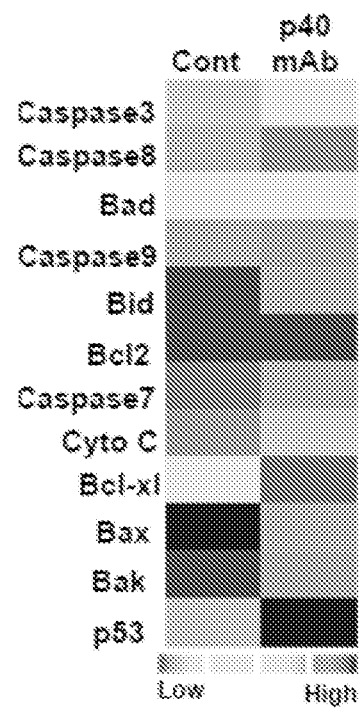
Figure 3F:
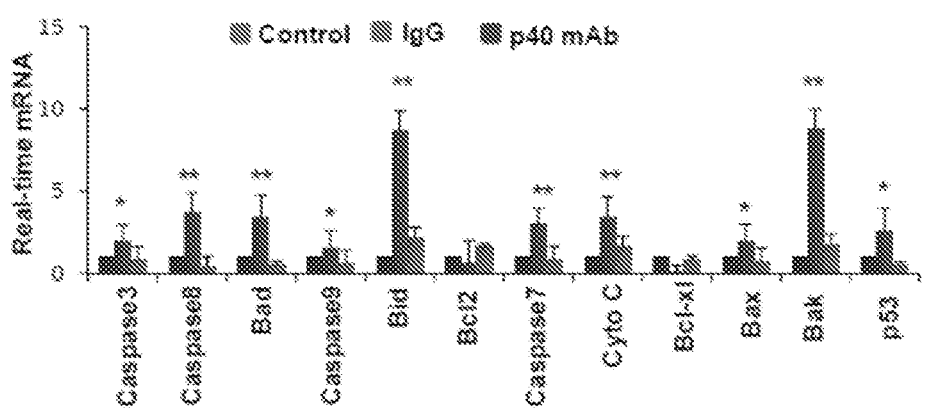

From the tumor regression curve, it was clear that the size of tumors in p40 mAb-treated group decreased steadily and significantly as compared to both control and IgG-treated group (FIG. 3C). Next, we monitored apoptosis in these tumor tissues. Our TUNEL results clearly showed that the population of TUNEL-positive dead cells in the p40 mAb-treated tumors was higher than either control or IgG-treated tumors (FIG. 3D), suggesting that the neutralization of p40 by p40 mAb is capable of inducing apoptosis in tumor tissues. To further confirm this finding, we monitored the mRNA expression of different apoptotis-related genes in treated and untreated tumor tissues using custom gene array. Gene array (FIG. 3E) followed by real-time PCR analysis of individual genes (FIG. 3F) clearly indicated that p40 mAb treatment significantly elevated the expression of apoptotis-related different genes such as caspases 3, caspase 7, caspase 8, caspase 9, BAD, BID, cytochrome C, BAK, and p53. Taken together, these results suggest that the neutralization of p40 induces apoptosis in vivo in prostate tumor cells.

Figure 4A:
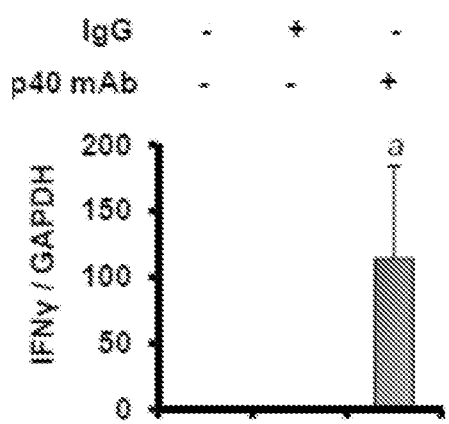
FIG. 4: Role of IFNγ in p40 mAb-mediated death of TRAMP cells. (A) Real-time PCR analysis for mRNA expression of control, IgG, and p40 mAb-treated TRAMP cells. $^a$$p<0.01$ vs. control. (B) ELISA for the protein expression of IFNγ in control, IgG, and p40 mAb-treated TRAMP cells. $^a$$p<0.01$ vs. 48 hr control and $^b$$p<0.001$ vs. 72 hr control. (C) IL-10 ELISA assay in supernatants of IgG and p40 mAb-treated TRAMP cells. $^a$$p<0.05$ vs. control. (D) TUNEL assay in control, p40 mAb-, IgG-, (p40 mAb+different doses of IFNγ-neutralizing Ab)-, (p40mAb+IgG)-, and IFNγ-Ab-treated TRAMP cells. (E) LDH and (F) MTT assays in TRAMP cells. Results are mean±SD of three different experiments. $^a$$p<0.001$ vs. control and $^b$$p<0.01$ vs. p40 mAb-treated cells.
Figure 4B:
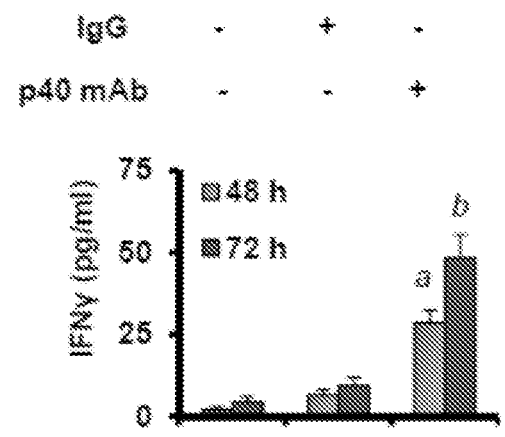
Figure 4C:
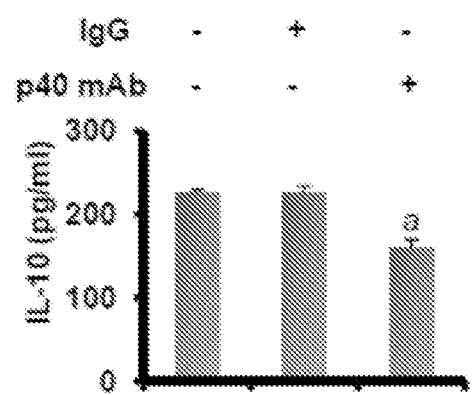
Figure 4D:
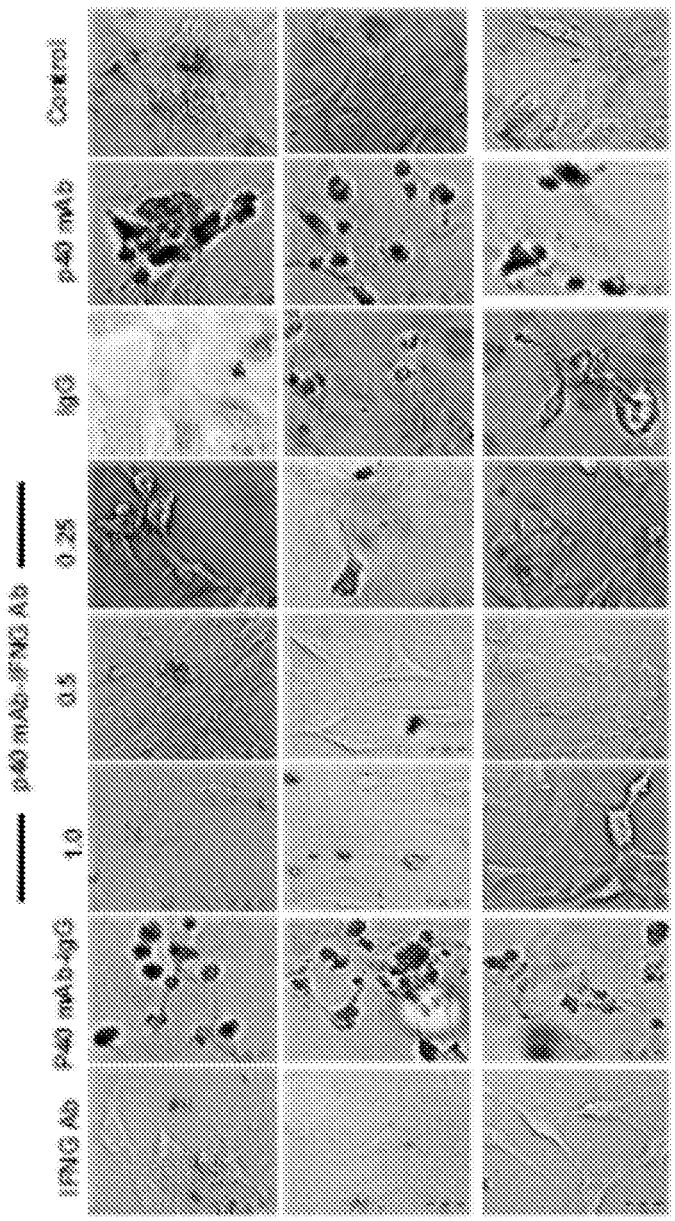
Figure 4E:
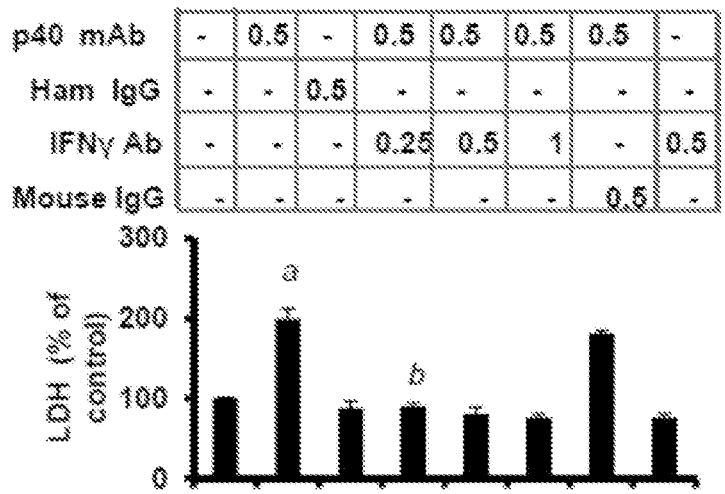
Figure 4F:
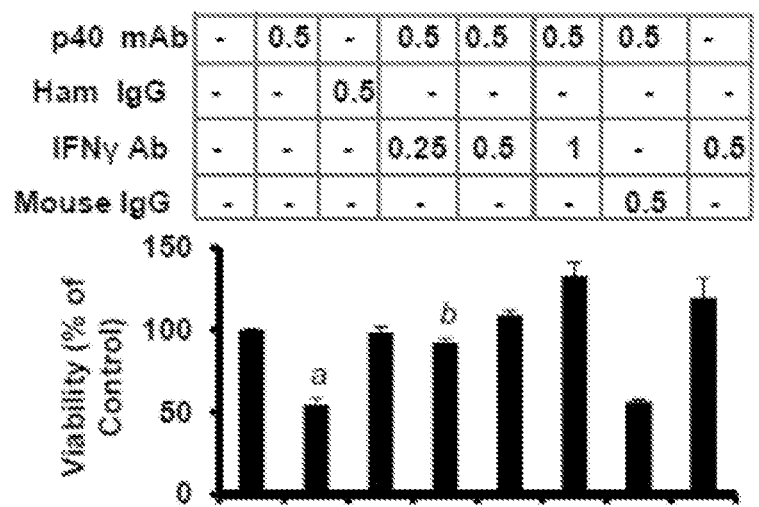
Figure 6:
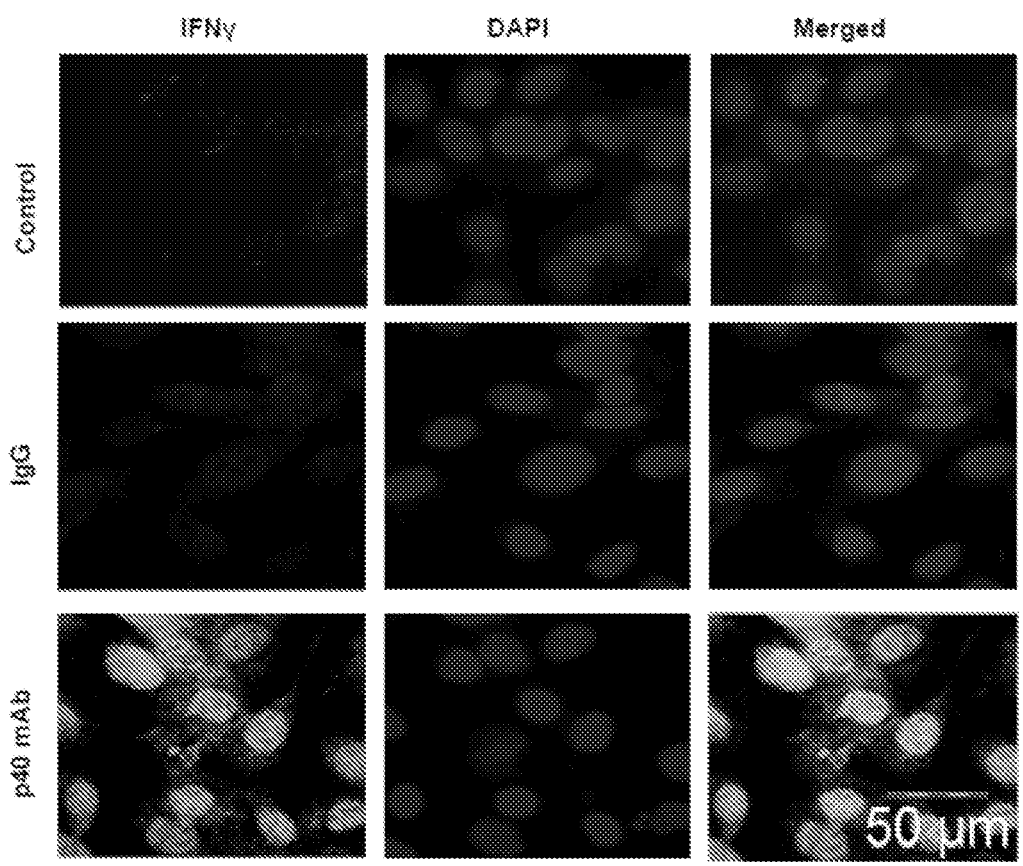
FIG. 6: Effect of p40 mAb on the expression of IFNγ protein in cultured TRAMP cells. Immunocytochemical analyses of IFNγ (green) in control, IgG-, and p40 mAb-treated TRAMP cells. Nuclei were stained with DAPI.
Figure 7A:
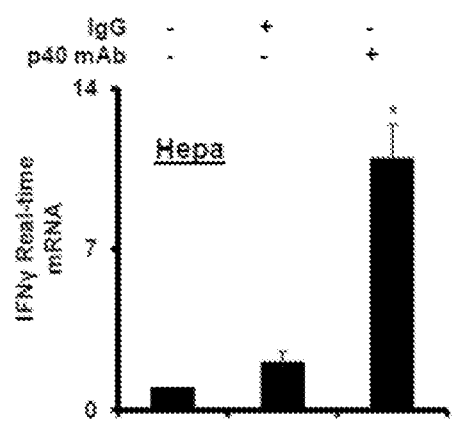
FIG. 7: Effect of p40 mAb on the expression of IFNγ in cultured Hepa and 4T1 cells. Real-time mRNA (A & C) and ELISA (B & D) analyses of IFNγ in control, IgG-, and p40 mAb-treated Hepa) (A & B) and 4T1 (C & D) cells. Results are mean±SD of three different experiments. *$p<0.05$ vs. control, and **$p<0.001$ vs. control.
Figure 7B:
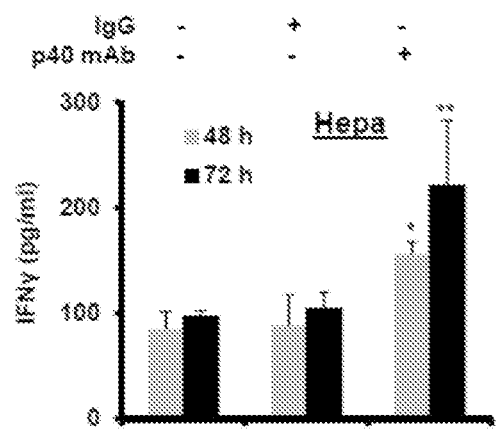
Figure 7C:
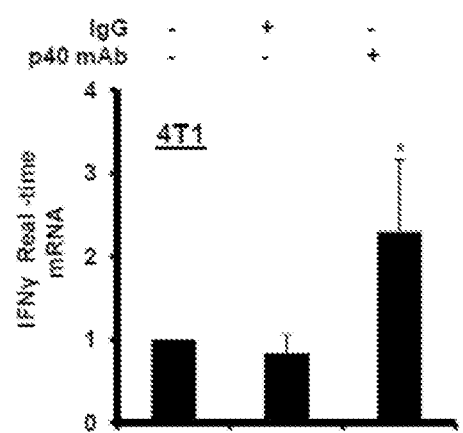
Figure 7D:
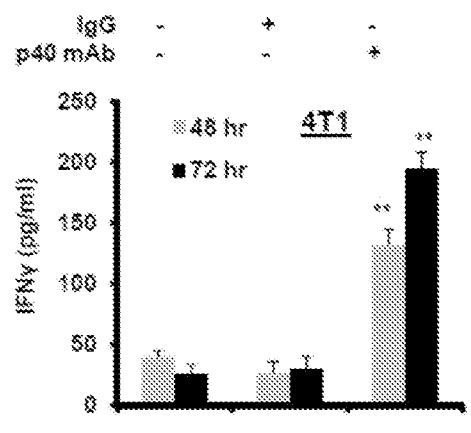
Figure 8A:
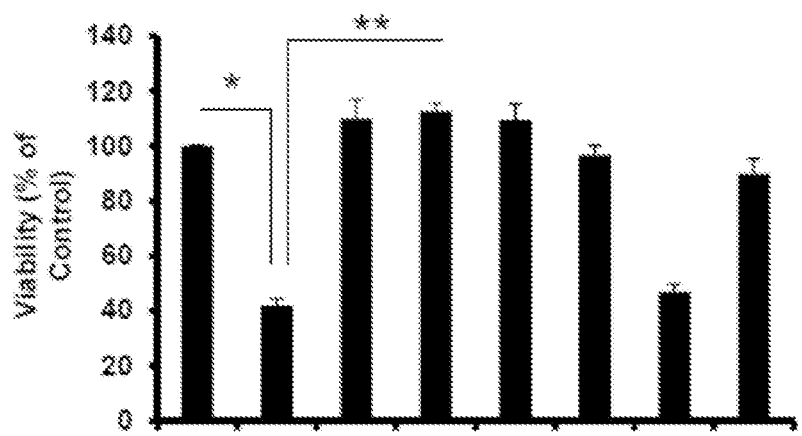
FIG. 8: Role of IFNγ in p40 mAb-mediated death in Hepa cells. (A) MTT and (B) LDH assays were performed in p40 mAb-(0.5 μg/mL) or p40 mAb together with increasing doses of IFNγ Ab (0.25, 0.5, and 1 μg/mL)-treated Hepa cells. Results are mean±SD of three different experiments. *$p<0.001$ vs. control, and **$p<0.001$ vs. p40 mAb only.
Figure 8B:
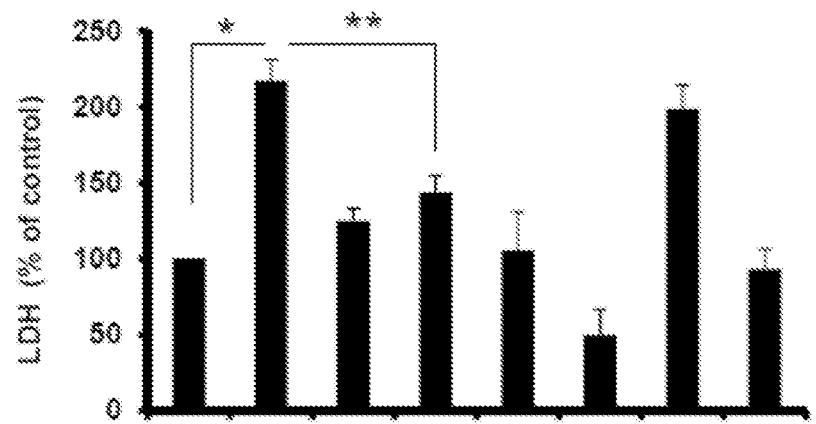
Figure 9A:
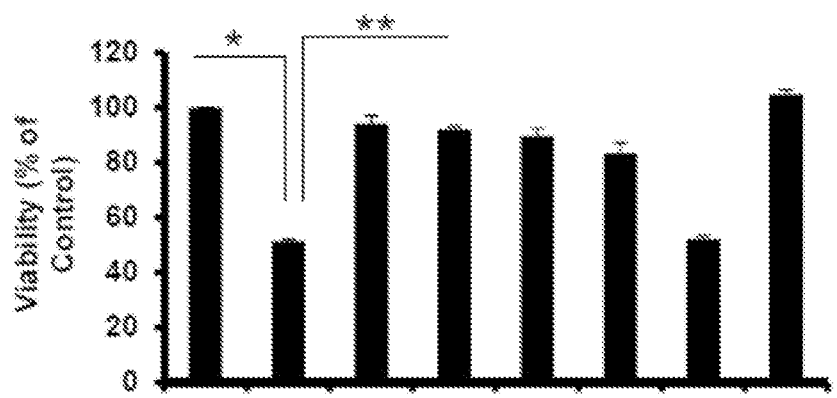
FIG. 9: Role of IFNγ in p40 mAb-mediated death in 4T1 cells. (A) MTT and (B) LDH assays were performed in p40 mAb-(0.5 μg/mL) or p40 mAb together with increasing doses of IFNγ Ab-treated 4T1 cells. Results are mean±SD of three different experiments. *$p<0.001$ vs. control, and **$p<0.001$ vs. p40 mAb only.
Figure 9B:
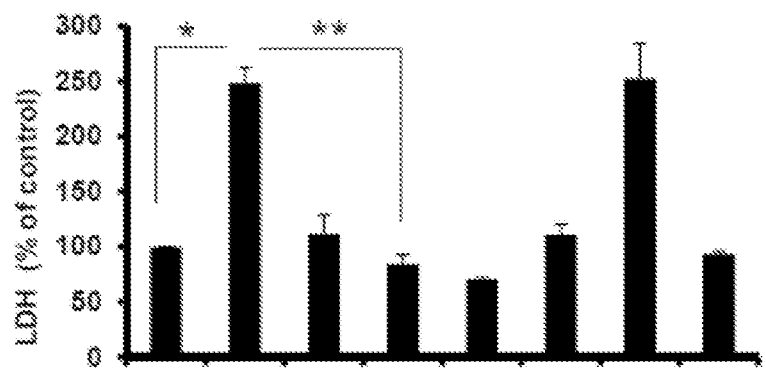

Example 4: Specific Neutralization of p40 Stimulates the Production of IFN-γ in Cultured Tumor Cells and In Vivo in Tumor Tissue Next, we investigated mechanism by which p40 mAb induced death response in cancer cells. Induction of IFN-γ production is a proven therapeutic strategy to induce cytotoxicity in cancer cells (13). Therefore, we examined if p40 mAb treatment is capable of upregulating the expression of IFN-γ in TRAMP tumor cells. We observed that p40 mAb, but not IgG, significantly upregulated the mRNA expression of IFN-γ in cultured TRAMP cells (FIG. 4A). Although IFN-γ is a Th1 cell cytokine, our ELISA results (FIG. 4B) and immunocytochemical analysis (FIG. 6) clearly indicated that p40 mAb-treatment increased the level of IFNγ in TRAMP cells. On the other hand, p40 mAb treatment (FIG. 4C) decreased the level of IL-10, an anti-inflammatory cytokine that is known to support the growth of cancer cells (14). Next, we investigated if the elevated expression of IFNγ in p40 mAb-treated TRAMP cells was indeed involved in the cell death. Therefore, we treated TRAMP cells with IFNγ neutralizing antibody either alone or together with p40 mAb. TUNEL (FIG. 4D), LDH (FIG. 4E), and MTT (FIG. 4F) assays revealed that IFNγ neutralizing antibody abrogated p40 mAb mediated cell death in TRAMP cells. These results were specific as IgG was unable to protect the p40 mAb-mediated cell death in TRAMP cells (FIG. 4D-F). Other tumor cells including Hepa (FIGS. 7A-B) and 4T1 (FIG. S2C-D) also displayed upregulated expression of IFNγ. Similar to TRAMP cells, our MTT viability assay (FIGS. 8A & 9A) and LDH release assay (FIGS. 8B & 9B) revealed that p40 mAb, but not IgG, significantly stimulated death in both Hepa and 4T1 tumor cells, suggesting that neutralization of p40 could be crucial in inducing death of different tumor cells.

Figure 10A:
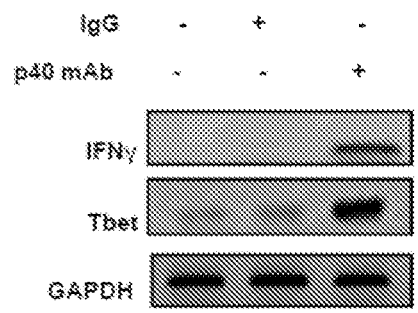
FIG. 10: Effect of p40 mAb on the expression of IFN-γ in TRAMP tumor tissue. (A) Semi-quantitative RT-PCR analyses to monitor the mRNA expression of IFN-γ, t-bet, IL-10, GATA-3, and Foxp3 in control, p40 mAb-, and IgG-treated TRAMP tumor tissue. (B) Real-time PCR and (C) ELISA analyses were performed to confirm the level of IFN-γ in different treatment groups. $^a$$p<0.001$ vs. control. (D) Semi-quantitative RT-PCR analyses to monitor the mRNA levels of IL-10, GATA-3, and Foxp3 in control, p40 mAb-, and IgG-treated TRAMP tumor tissue. (E) Real-time PCR of IL-10 and Foxp3 and (F) ELISA analyses of IL-10 were performed to confirm our results in different treatment groups. $^a$$p<0.001$ vs. control. Immunohistochemical analyses of (G) IFNγ (green) and (H) t-bet (Red) in different groups of tumor tissues. Results represent analysis of two sections of each of five mice per group.
Figure 10B:
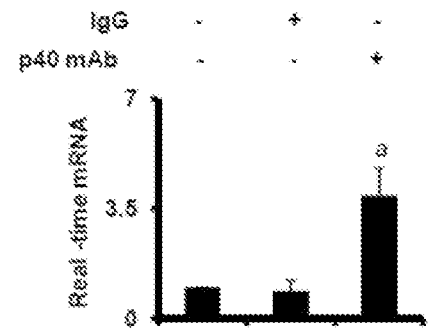
Figure 10C:
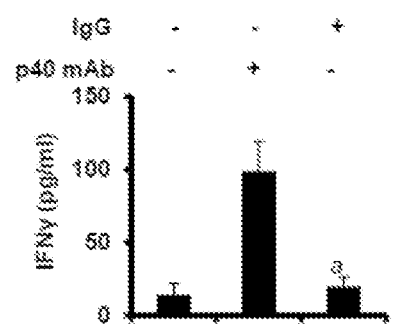
Figure 10D:
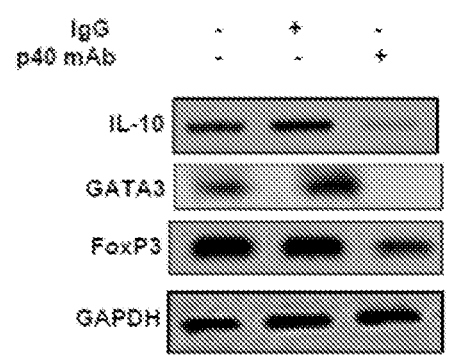
Figure 10E:
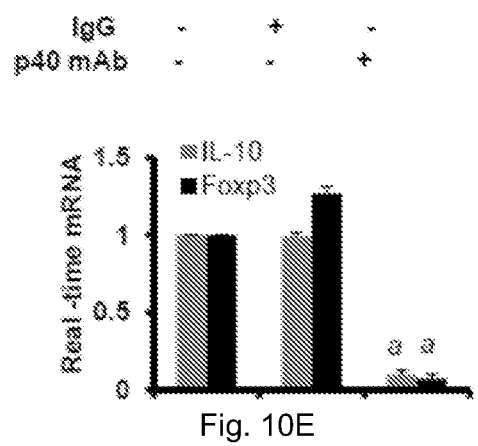
Figure 10F:
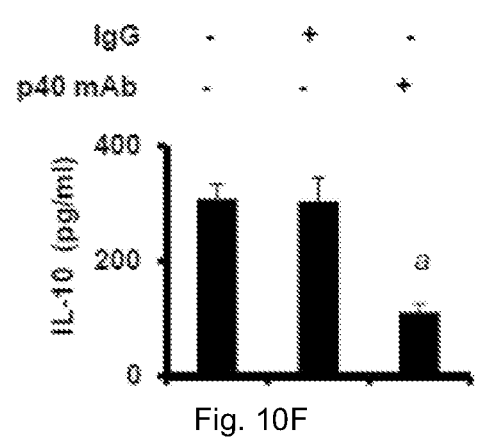
Figure 10G:
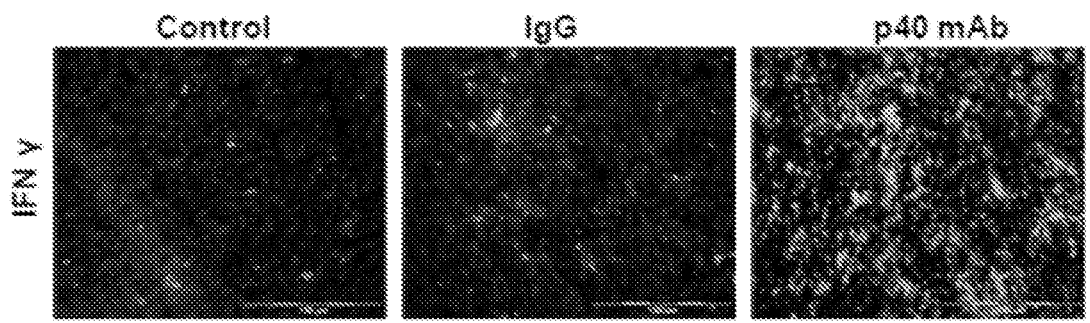
Figure 10H:
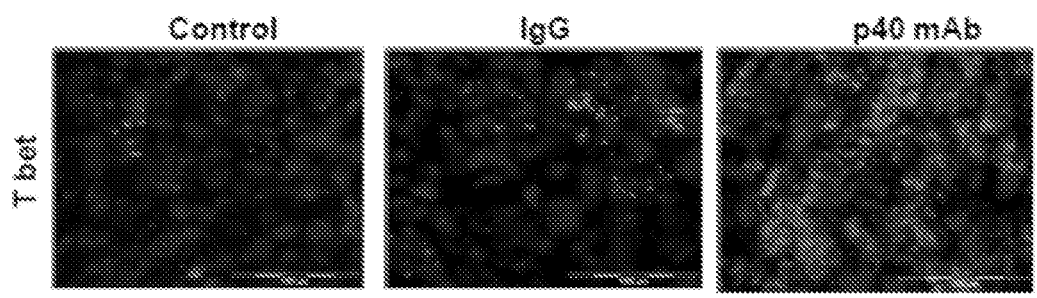

When analyzing the level of IFNγ in tumor tissue, we also observed that similar to cell culture data, p40 mAb-treated tumor tissue expressed more IFNγ mRNA (FIGS. 10A-B) and protein (FIGS. 10C & 10G) compared to control and IgG-treated tumors. Moreover, the expression of T-bet, IFNγ inducing transcription factor, was also found to be upregulated in the tumor of p40 mAb-treated, but not control and IgG-treated, mice (FIG. 10H). Since the upregulation of IL-10 (15) and the regulatory T cell marker Foxp3 (16) are believed to inhibit the cytotoxic effects in cancer cells, we also monitored these molecules in tumor tissue. Interestingly, the expression of IL-10, GATA-3 and Foxp3 decreased in p40 mAb treated tumors as compared to control and IgG treated tumor (FIG. 10D-F). These results suggest that neutralization of p40 is capable of inducing cell-mediated immunity and down-regulating humoral immunity and Tregs in cultured TRAMP cells and in vivo in TRAMP tumor tissue.

Figure 11A:
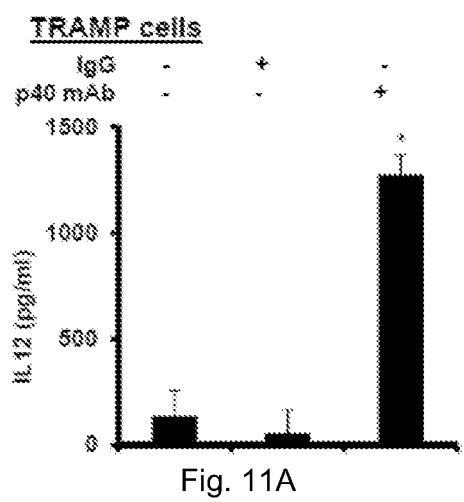
FIG. 11: Effect of p40 mAb on the expression of IL-12 in cultured TRAMP cells and TRAMP tumor tissue. (A) ELISA analyses to monitor the levels of IL-12 in cultured TRAMP cells treated with p40 mAb (0.5 μg/mL), and mouse IgG (0.5 μg/mL) for 24 hrs under serumfree condition. Results are mean±SD of three different experiments. *$p<0.001$ vs. control. (B) Similarly, IL-12 level was monitored in TRAMP tumor tissue (n=3) treated with saline, p40mAb, and IgG. Results are mean±SEM of three mice per group. *$p<0.001$ vs. control.
Figure 11B:
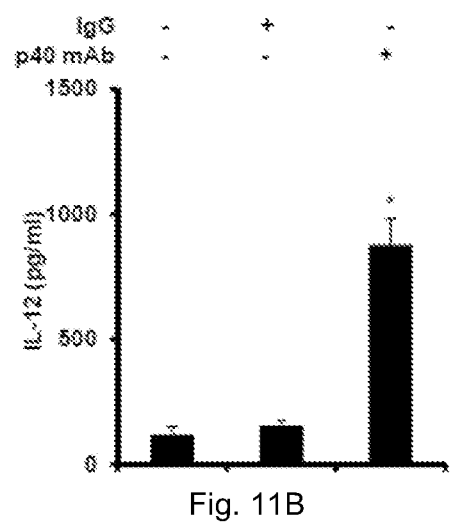
Figure 12A:
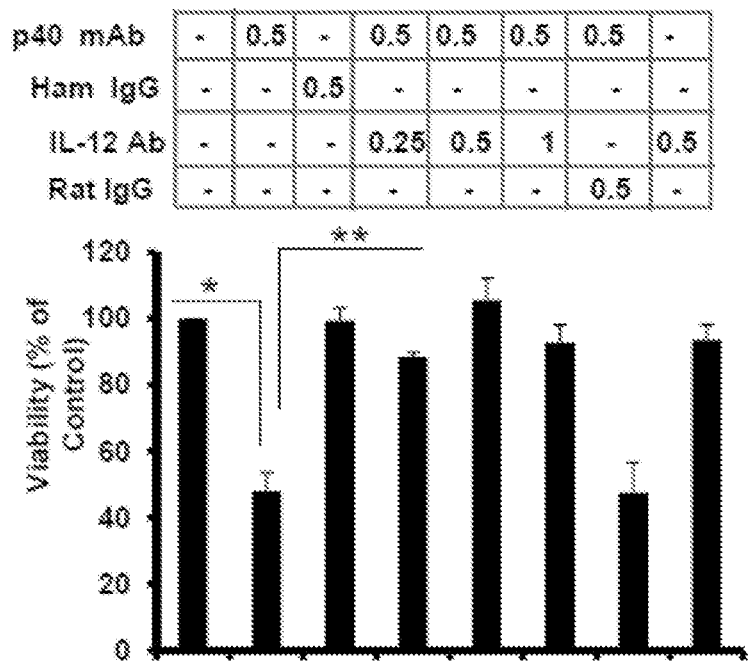
FIG. 12: Role of IL-12 in p40 mAb-mediated death in TRAMP cells. (A) MTT and (B) LDH assays were performed in p40 mAb-(0.5 µg/mL) or p40 mAb together with increasing doses of IL-12 Ab-treated TRAMP cells. Results are mean±SD of three different experiments. *p<0.001 vs. control, and **p<0.001 vs. p40 mAb only.
Figure 12B:
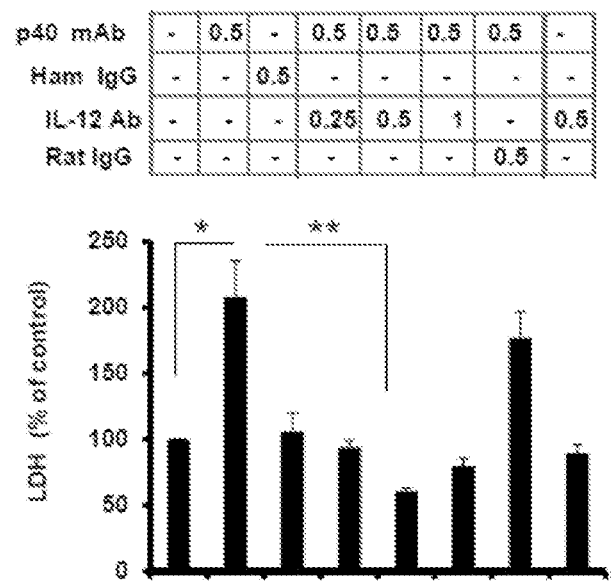

Example 5: Specific Neutralization of p40 Induces IL-12 Production in TRAMP Tumor Cells The upregulation of IFN-γ is achieved by the activation of IL-12 signaling pathway (13, 17). Since p40 mAb increased the production of IFN-γ and induced death in TRAMP cells via IFN-γ, we investigated the involvement of IL-12 in these processes. The production of IL-12 markedly increased in p40 mAb-treated TRAMP cells (FIG. 11A) and in vivo in tumor tissue (FIG. 10B) as compared to control and IgG-treatment, suggesting that IL-12 signaling pathway could be involved in p40 mAb-mediated IFN-γ production and cell death. We found that neutralization of IL-12 by functional blocking antibodies suppressed p40 mAb-induced production of IFN-γ in TRAMP cells (data not shown). Furthermore, neutralizing antibodies against IL-12 abrogated p40 mAb-mediated death of TRAMP cells as indicated MTT (FIG. 12A) and LDH release (FIG. 12B). These results suggest that neutralization of p40 induces IFN-γ and cell death in cancer cells via IL-12 signaling pathway.

Figure 5B:
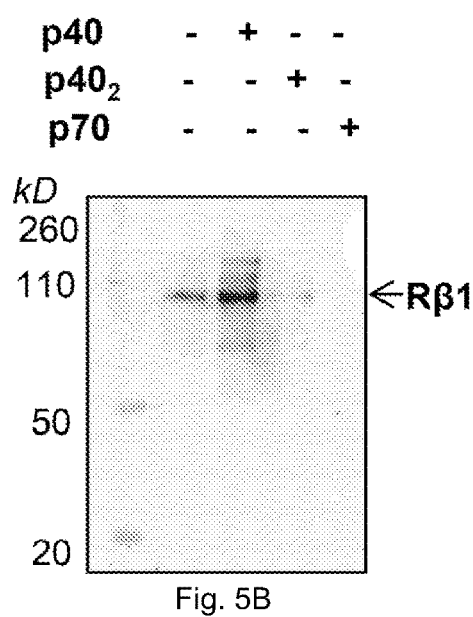
FIG. 5: Neutralization of p40 by mAb stimulates the internalization of IL-12Rβ1 in TRAMP tumor cells. Cells were treated with p40 (20 ng/mL), p402 (20 ng/mL), p70 (20 ng/mL), p40 mAb (0.5 μg/mL), and mouse IgG (0.5 μg/mL) for 2 hrs in serum-free condition followed by FACS analyses of IL-12Rβ1 in control (i), p40_ (ii), p40$_2$_ (iii), p70_ (iii), p40 mAb-(iv), and IgG-(v) treated TRAMP cells. Immunoblot analyses of membrane-bound IL-12Rβ1 (B), pan Cadherin (pCAD) (C), and total IL-12Rβ1 (D) in p40-, p40$_2$-, p70-, p40 mAb-, and IgG-treated TRAMP cells. Immunoblot analyses of membrane-bound IL-12Rβ1 (E), pCAD (F), and total IL12Rβ1 (G) in p40 cytokine- and p40 mAb-treated TRAMP cells. Results represent three independent experiments. Immunoblot analyses of IL-12Rβ1 (H) in the membrane fraction of p40 mAb-treated TRAMP cells pretreated with either 5 μM filipin (caveolin inhibitor) or 2 μM chloropromazine (CPM; clathrin inhibitor) for 2 hrs under serum-free condition. Immunoblot results were normalized with pCAD immunoblot (bottom panel). (I) Relative density of immunoblot analyses normalized with pCAD. Results are mean±SD of three different experiments. *$p<0.001$ vs. p40 mAb. Immunocytochemical analyses of IL-12 Rβ1 (Red), and caveoiln-1 (Cav-1; green) in (J) control, (K) p40 mAb, (L) (p40 mAb+filipin)-treated TRAMP cells. Nuclei were stained with DAPI. (M) Schematic presentation by which neutralization of p40 induces cell-mediated immunity in TRAMP cells.
Figure 5C:
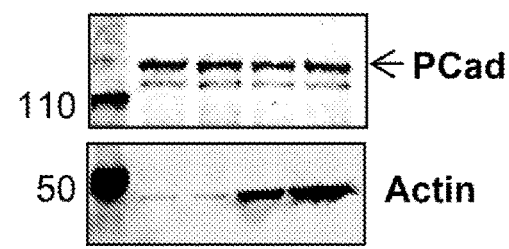

Example 6: Selective Neutralization of p40 Induces the Internalization of IL-12Rβ1 in TRAMP Cells The IL-12 signaling pathway is initiated by the interaction between IL-12 and IL-12 receptor, which is a heterodimer of IL-12Rβ1 and IL-12Rβ2. A functional IL-12 receptor has been reported to be internalized after successful binding with its ligand IL-12 (18), otherwise it stays arrested in the membrane. Therefore, we examined if p40 monomer was involved in the arresting of IL-12 receptor in TRAMP cells in order to negate the IL-12 signaling pathway. Our FACS analyses revealed that the treatment with p40, but neither p40$_2$ nor p70, increased the surface expression of IL-12Rβ1 in TRAMP cells (FIG. 5Ai-iv). On contrary, p40 did not have any effect on the surface expression of IL-12Rβ2 (FIG. 13). Furthermore, treatment with p40 mAb, but not IgG, down-regulated the membrane level of IL-12Rβ1 (FIG. 5Av & vi), suggesting the involvement of p40 in the arresting of IL-12Rβ1 on the membrane. To further confirm, we performed immunoblot analyses of IL-12Rβ1 in the membrane fraction of TRAMP cells treated with p40, p402, or p70, separately. Interestingly, we found that treatment with p40, but neither $p40_2$ nor IL-12, increased the presence of IL-12Rβ1 in the membrane (FIG. 5B). Pan-cadherin was analyzed to check the purity of the membrane fraction (FIG. 5C; top panel). Surprisingly, we found increased level of β-actin in membrane fractions of p402- and p70-treated TRAMP cells, suggesting that the treatment with p402 or p70 is possibly associated with increased formation of endocytic vesicles in the membrane (FIG. 5C; bottom panel). In contrast, we did not observe increased membrane level of β-actin in p40-treated TRAMP cells (FIG. 5C). These results suggest that p40, but neither $p40_2$ nor p70, may be involved in the arresting of IL-12Rβ1 in the membrane.

Figure 5D:
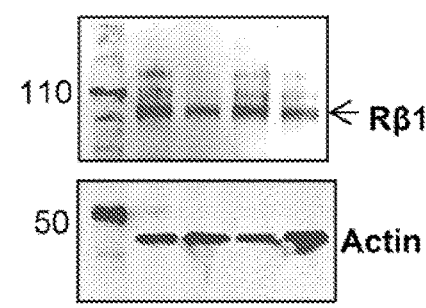
Figure 5E:
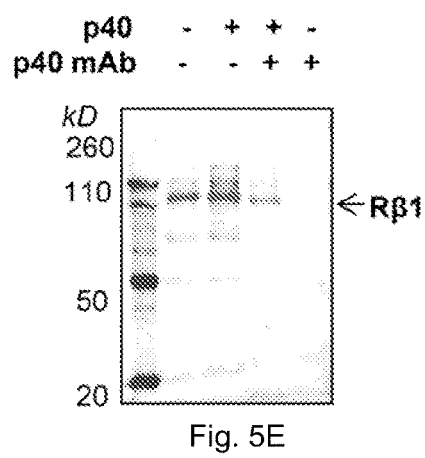
Figure 5F:
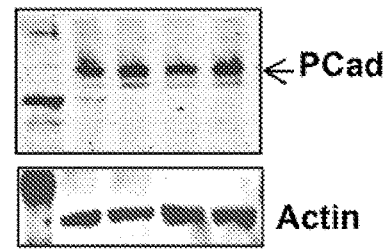
Figure 5G:
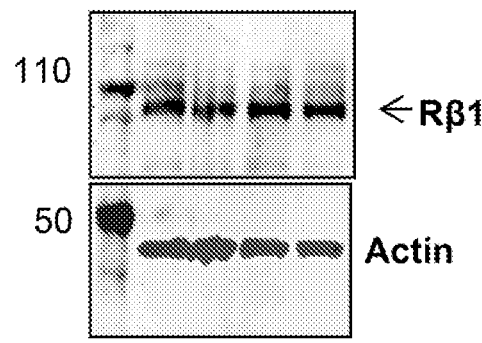

However, there was no difference in IL-12Rβ1 in whole cell extract when TRAMP cells were treated with these cytokines (FIG. 5D), negating the possibility of induction of IL-12Rβ1 level by p40 monomer. Consistently, the p40 mAb abrogated p40-mediated increase in IL-12Rβ1 in membrane of TRAMP cells (FIG. 5E), suggesting that p40 is indeed involved in the membrane arrest of IL-12Rβ1. Pan-Cadherin was analyzed to monitor the purity of the membrane fraction (FIG. 5F; top panel). The level of β-actin was higher in p40 mAb-treated cells, suggesting that the absence of p40 may induce the formation of endocytic vesicles in TRAMP cells (FIG. 5F; bottom panel). However, again, there was no difference in the level of total IL-12Rβ1 between (p40+p40 mAb)-treated cells and p40-treated cells, suggesting that p40 mAb treatment does not down-regulate the expression of IL-12Rβ1 in TRAMP cells. Together, these results suggest that excess p40 released by TRAMP cells inhibit IL-12 signaling by suppressing the internalization or endocytosis of IL-12Rβ1.

Figure 5H:
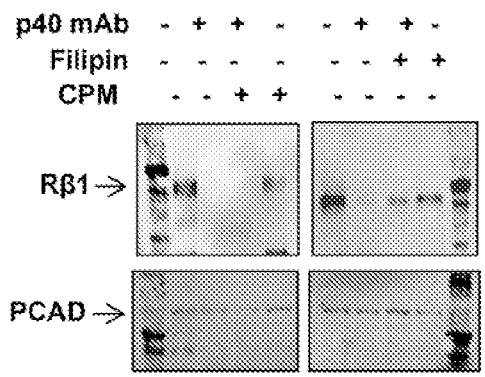
Figure 5I:
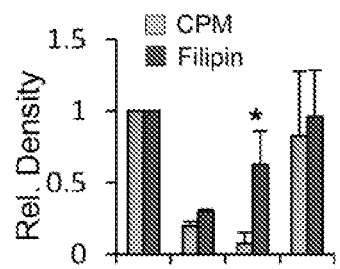
Figure 5M:
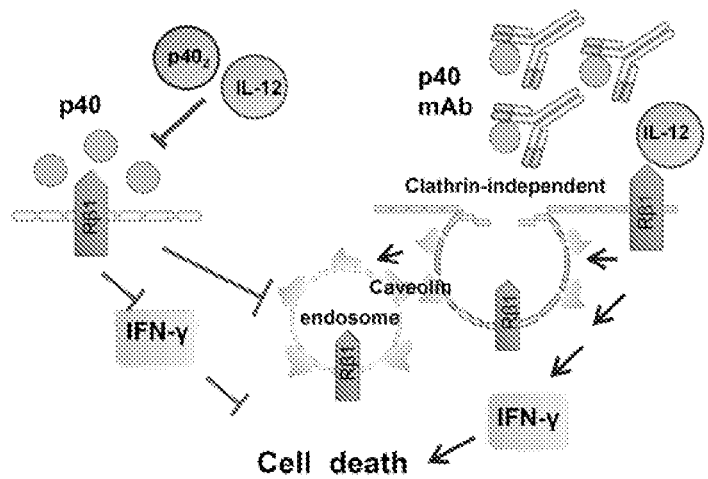
Figure 5J:
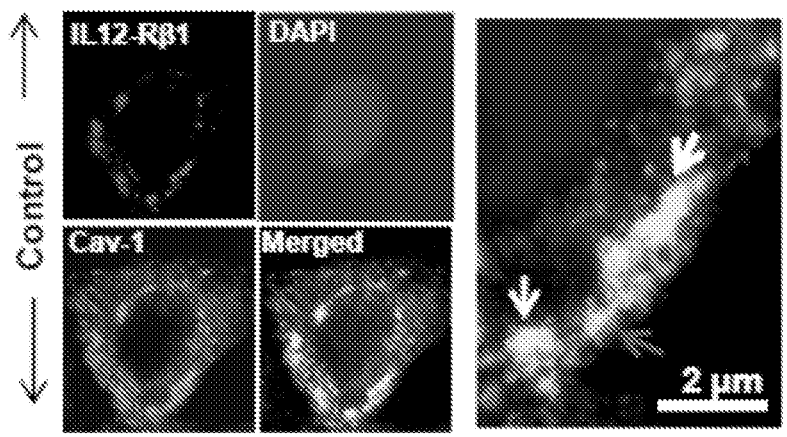
Figure 5K:
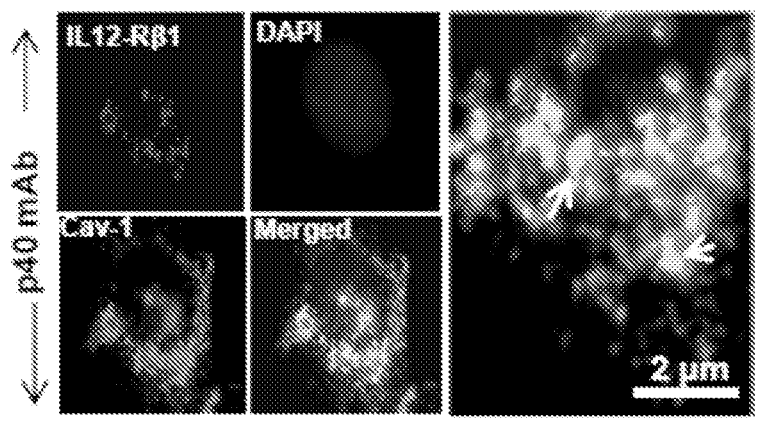
Figure 5L:
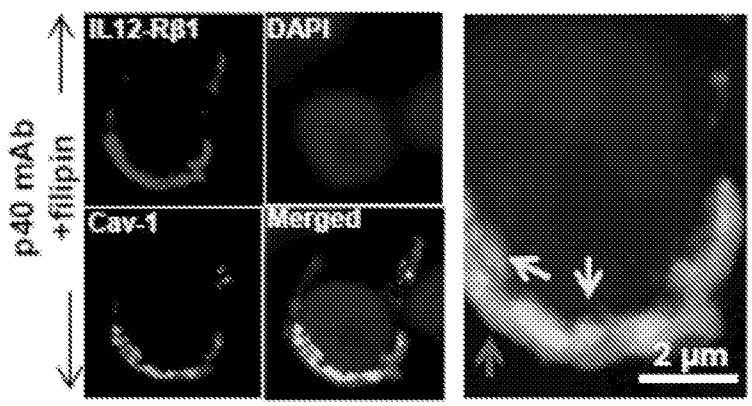

Next, we investigated mechanisms by which neutralization of p40 induced the internalization of IL-12Rβ1. Receptor internalization primarily happens via two mechanisms—clathrin-dependent and caveolin-dependent. To examine the involvement of clathrin or caveolin, we used two pharmacological inhibitors filipin and chlorpromazine (CPM). Interestingly, pre-treatment with filipin, but not CPM, significantly inhibited the membrane internalization of IL-12Rβ1 in p40 mAb-treated TRAMP cells (FIGS. 5H & 5I), suggesting that p40-mediated internalization of IL 12Rβ1 occurs via caveolin-sensitive and clathrin-independent pathway. Immunofluorescence analysis further confirmed that the p40 mAb-mediated internalization of IL-12Rβ1 in TRAMP cells is caveolin-dependent (FIG. 5J-L) as neutralizing p40 with p40 mAb was unable to internalize IL-12Rβ1 when TRAMP cells were pretreated with filipin (FIG. 5L).

Under the provisions of the Budapest Treaty on the International Recognition of the Deposit of Microorganisms for the purpose of Patent Procedure, Applicant has deposited biological material comprising twenty-five (25) vials of hybridoma with the designation of antibody (mAb) a3-3a and twenty-five (25) vials of hybridoma with the designation of antibody (mAb) a3-7g with the International Depository Authority, American Type Culture Collection (ATCC) of 1080 University Blvd., Manassas, Va. 20110-2209. The mAb a3-3a was deposited on Aug. 18, 2021 and assigned deposit number PTA-127109. The mAb a3-7g was deposited on Sep. 15, 2021 and assigned deposit number PTA-127131. The deposited hybridomas comprise monoclonal antibodies against the p40 monomer which comprises mAb a3-3a or mAb a3-7g.

TABLE 1

Antibodies: IF, immunofluorescence; WB, Western blot; FACS, fluorescence-activated cell sorting; IC, immunocytochemistry; BL, blocking

| Antibody | Manufacturer | Catalog | Host | Application | Dilution |
|---|---|---|---|---|---|
| IFNγ | eBioscience | 16-7311-81 | Rat | Blocking, IF | 0.25-1 µg/mL (BL), 1:100 (IF) |
| Tbet | Santacruz | sc-21003 | Rabbit | IF | 1:100 |
| IL-12 | eBioscience | 16-7123-81 | Rat | Blocking | 0.25-1 µg/mL (BL) |
| IL-12Rβ1 | BD Bioscience (PE-tagged) | 551974 | Mouse | FACS | 0.5-1 µg/$10_6$ cells |
|  | Santacruz | sc-658 | Rabbit | WB | 1:200 |
| IL-12Rβ2 | BD Bioscience | 552819 | Hamster | FACS | 0.5-1 µg/$10_6$ cells |
| Caveolin-1 | Cell Signaling Technology | 3238 | Rabbit | WB, IC | 1:1000 (WB) 1:400 (IC) |
| Clathrin | Cell Signaling Technology | 2410 | Rabbit | WB | 1:1000 |
| P-cadherin | Cell Signaling Technology | 4068 | Rabbit | WB | 1:1000 |
| β-actin | Abcam | ab6276 | Mouse | WB | 1:2000 |

TABLE 2

List of primers

| Gene | Directions | Sequence (5' . . . 3') |
|---|---|---|
| IFNγ | Sense | CGGCACAGTCATTGAAAGCC (SEQ ID NO.: 1) |
|  | Antisense | TGCATCCTTTTTCGCCTTGC (SEQ ID NO.: 2) |
| IL10 | Sense | TAAGGCTGGCCACACTTGAG (SEQ ID NO.: 3) |
|  | Antisense | GTTTTTCAGGGATGAAGCGGC (SEQ ID NO.: 4) |

TABLE 2-continued

List of primers

| Gene | Directions | Sequence (5'...3') |
|---|---|---|
| Tbet | Sense | ATTGGTTGGAGAGGAAGCGG (SEQ ID NO.: 5) |
| | Antisense | TGTGCACCCTTCAAACCCTT (SEQ ID NO.: 6) |
| GATA3 | Sense | TGGCGCCGTCTTGATAGTTT (SEQ ID NO.: 7) |
| | Antisense | CCTCTTCCGTCAGCGGATAC (SEQ ID NO.: 8) |
| Foxp3 | Sense | TGTGCCTGGTATATGCTCCC (SEQ ID NO.: 9) |
| | Antisense | GTTCTTGTCAGAGGCAGGCT (SEQ ID NO.: 10) |
| GAPDH | Sense | GCATCTTCTTGTGCAGTGCC (SEQ ID NO.: 11) |
| | Antisense | TACGGCCAAATCCGTTCACA (SEQ ID NO.: 12) |
| PDL-1 | Sense | TCACTTGCTACGGGCGTTTA (SEQ ID NO.: 13) |
| | Antisense | TGCCAATCGACGATCAGAGG (SEQ ID NO.: 14) |
| PDL-2 | Sense | GGTGTGTGATTGGTAGGCCA (SEQ ID NO.: 15) |
| | Antisense | CATCCAGCAGGTAACCAGGG (SEQ ID NO.: 16) |
| PD-1 | Sense | ATCTACCTCTGTGGGGCCAT (SEQ ID NO.: 17) |
| | Antisense | GAGTGTCGTCCTTGCTTCCA (SEQ ID NO.: 18) |
| CTLA-4 | Sense | TACTCTGCTCCCTGAGGACC (SEQ ID NO.: 19) |
| | Antisense | CCGTGTCAACAGGTCTCAGT (SEQ ID NO.: 20) |
| Cytochrome C | Sense | CCCCCAGCCTCCCTTATCTT (SEQ ID NO.: 21) |
| | Antisense | GGTCTGCCCTTTCTCCCTTC (SEQ ID NO.: 22) |
| Caspase 3 | Sense | GAGCTTGGAACGGTACGCTA (SEQ ID NO.: 23) |
| | Antisense | CCGTACCAGAGCGAGATGAC (SEQ ID NO.: 24) |
| Caspase 8 | Sense | AACATTCGGAGGCATTTCTGT (SEQ ID NO.: 25) |
| | Antisense | AGAAGAGCTGTAACCTGTGGC (SEQ ID NO.: 26) |
| Caspase 7 | Sense | TTTTCCCAAAGCTGCCCTCG (SEQ ID NO.: 27) |
| | Antisense | GCGTCAATGTCGTTGATGGG (SEQ ID NO.: 28) |
| Caspase 9 | Sense | CTCTGAAGACCTGCAGTCCC (SEQ ID NO.: 29) |
| | Antisense | CTGCTCCACATTGCCCTACA (SEQ ID NO.: 30) |
| P53 | Sense | ACCAGGGCAACTATGGCTTC (SEQ ID NO.: 31) |
| | Antisense | AGTGGATCCTGGGGATTGTG (SEQ ID NO.: 32) |
| BAD | Sense | CAGCGTACGCACACCTATCC (SEQ ID NO.: 33) |
| | Antisense | CGGGATCGGACTTCCTCAAG (SEQ TD NO.: 34) |
| BID | Sense | TCTGAGGTCAGCAACGGTTC (SEQ ID NO.: 35) |
| | Antisense | TTTGTCTTCCTCCGACAGGC (SEQ ID NO.: 36) |
| BAX | Sense | CTGGATCCAAGACCAGGGTG (SEQ ID NO:: 37) |
| | Antisense | CCTTTCCCCTTCCCCCATTC (SEQ ID NO.: 38) |
| BCL2 | Sense | AGCATGCGACCTCTGTTTGA (SEQ ID NO.: 39) |
| | Antisense | GCCACACGTTTCTTGGCAAT (SEQ ID NO.: 40) |
| BCL-XL | Sense | TTGTACCTGCTTGCTGGTCG (SEQ ID NO.: 41) |
| | Antisense | CCCGGTTGCTCTGAGACATT (SEQ ID NO.: 42) |
| BAK | Sense | CCTGGGCCAACACGC (SEQ ID NO.: 43) |
| | Antisense | CTGTGGGCTGAAGCTCTTTTCTA (SEQ ID NO.: 44) |

Example 7—Levels of p40, p40₂ and IL-2 in Human Patients

Table 3 shows serum levels of p40, p40$_2$ and IL-12 measured using ELISA in 11 prostate cancer patients and 11 control subjects. Concentrations of p40 and p402 were measured in serum of prostate cancer patients and healthy controls by a sandwich ELISA as described in Hybridoma 27: 141-151, 2008; J. Immunol. 182: 5013-5023, 2009. Briefly, for quantifying p40, we used mAb a3-3a for coating and mAb a3-7 g for detection. Similarly, for measuring p40$_2$, mAb a3-1d and mAb d7-12c were used for coating and detection, respectively. Levels of IL-12 in serum were measured using the IL-12 ELISA kit from eBioscience (San Diego, Calif. 92121).

Each level reported in Table 3 is an average of three measurements. The serum levels of p40 monomer are higher in the prostate cancer patients as compared to the control subjects. The results suggest that excess p40 may play a role in the pathogenesis of prostate cancer and that treatment of cancer patients with the monoclonal antibody against p40 monomer may inhibit/stop the progression of the prostate cancer.

TABLE 3

Levels of p40, p40$_2$ and IL-12 in serum of prostate cancer patients and control subjects

| Samples | Age | Race/Ethnicity | Gleason score | PSA (ng/ml) | Stage | p40 (pg/ml) | p40$_2$ (pg/ml) | IL-12 (pg/ml) |
|---|---|---|---|---|---|---|---|---|
| PC-1 | 55 | White | 6-7 | 13.15 | III | 3471 ± 318 | −96 ± 14 | 4 ± 0.4 |
| PC-2 | 58 | Asian | 8-9 | 42.4 | III | 2962 ± 732 | 330 ± 290 | 4 ± 0.084 |
| PC-3 | 56 | White | 8-9 | 28.1 | III | 4246 ± 1272 | 618 ± 478 | 6 ± 1.76 |
| PC-4 | 67 | White | 7 | 22.48 | III | 3337 ± 2206 | 514 ± 68 | 3 ± 0.753 |
| PC-5 | 61 | White | 7-8 | 29.0 | III | 2799 ± 291 | −113 ± 90 | 3 ± 2.93 |
| PC-6 | 56 | White | 8-9 | 56.4 | III | 2494 ± 1251 | 454 ± 88 | 6 ± 2.49 |
| PC-7 | 60 | White | 8-9 | 24.6 | III | 3590 ± 1822 | −163 ± 3 | 3 ± 2.83 |
| PC-8 | 59 | Caucasian | 7 | 4 | IV | 3446 ± 1082 | −157 ± 96 | 4 ± 1.37 |
| PC-9 | 52 | White | 6 | 28.4 | II | 1490 ± 543 | −584 ± 273 | 4.9 ± 0.21 |
| PC-10 | 76 | Caucasian | 9 | 6.52 | IV | 3704 ± 1460 | −733 ± 90 | 5 ± 3.81 |
| PC-11 | 71 | Caucasian | NA | 102.79 | IV | 2184 ± 751 | −264 ± 98 | 7 ± 1.61 |
| Control-1 | 65 | White | Healthy | Healthy | Healthy | 1060 ± 855 | 1164 ± 328 | 3 ± 0.448 |
| Control-2 | 63 | White | Healthy | Healthy | Healthy | 1018 ± 333 | 729 ± 530 | 6 ± 0.097 |
| Control-3 | 83 | White | Healthy | Healthy | Healthy | 866 ± 540 | 2361 ± 235 | 3 ± 0.097 |
| Control-4 | 63 | White | Healthy | Healthy | Healthy | 863 ± 359 | 1991 ± 785 | 5 ± 0.98 |
| Control-5 | 61 | White | Healthy | Healthy | Healthy | 1055 ± 768 | 1884 ± 433 | 6 ± 0.098 |
| Control-6 | 57 | Hispanic | Healthy | Healthy | Healthy | 1198 ± 395 | 2148 ± 539 | 10 ± 1.69 |
| Control-7 | 70 | White | Healthy | Healthy | Healthy | 1343 ± 728 | 1765 ± 507 | 3 ± 0.53 |
| Control-8 | 67 | White | Healthy | Healthy | Healthy | 606 ± 401 | 1534 ± 634 | 6 ± 2.05 |
| Control-9 | 66 | White | Healthy | Healthy | Healthy | 1003 ± 293 | 1192 ± 325 | 6 ± 1.22 |
| Control-10 | 52 | Asian | Healthy | Healthy | Healthy | 865 ± 107 | 626 ± 200 | 10 ± 4.5 |

Serum samples were obtained from Discovery Life Sciences (Los Osos, CA).
Each sample was analyzed for p40, p40$_2$ and IL-12 three times by ELISA.
PC, Prostate cancer;
NA, not available;
p40, p40 monomer;
p40$_2$, p40 homodimer;
IL-12, interleukin-12 . . .

REFERENCES

1. Lin W W & Karin M (2007) J Clin Invest 117, 1175-1183.
2. Trinchieri G (1994) Blood 84, 4008-4027.
3. Cui J, Shin T, Kawano T, Sato H, Kondo E, Toura I, Kaneko Y, Koseki H, Kanno M, & Taniguchi M (1997) Science 278, 1623-1626.
4. Zitvogel L, Tahara H, Robbins P D, Storkus W J, Clarke M R, Nalesnik M A, & Lotze M T (1995) J Immunol 155, 1393-1403.
5. Gately M K, Renzetti L M, Magram J, Stern A S, Adorini L, Gubler U, & Presky D H (1998) Annu Rev Immunol 16, 495-521.
6. Brahmachari S & Pahan K (2009) J Immunol 183, 2045-2058.
7. Jana M, Dasgupta S, Pal U, & Pahan K (2009) Glia 57, 1553-1565.
8. Pahan K, Sheikh F G, Liu X, Hilger S, McKinney M, & Petro T M (2001) J Biol Chem 276, 7899-7905.
9. Jana M & Pahan K (2009) Mol Immunol 46, 773-783.
10. Jana M & Pahan K (2009) Immunology 127, 312-325.
11. Dasgupta S, Bandopadhyay M, & Pahan K (2008) Hybridoma (Larchmt) 27, 141-151.
12. Mondal S, Roy A, & Pahan K (2009) J Immunol 182, 5013-5023.
13. Nastala C L, Edington H D, McKinney T G, Tahara H, Nalesnik M A, Brunda M J, Gately M K, Wolf S F, Schreiber R D, Storkus W J, et al. (1994) J Immunol 153, 1697-1706.
14. Sato T, Terai M, Tamura Y, Alexeev V, Mastrangelo M J, & Selvan S R (2011) Immunol Res 51, 170-182.
15. Kopf M, Le Gros G, Bachmann M, Lamers M C, Bluethmann H, & Kohler G (1993) Nature 362, 245-248.
16. Hori S, Nomura T, & Sakaguchi S (2003) Science 299, 1057-1061.
17. Wysocka M, Kubin M, Vieira L Q, Ozmen L, Garotta G, Scott P, & Trinchieri G (1995) Eur J Immunol 25, 672-676.
18. Durali D, de Goer de Herve M G, Giron-Michel J, Azzarone B, Delfraissy J F, & Taoufik Y (2003) Blood 102, 4084-4089.
19. Tucker J A, Jochems C, Gulley J L, Schlom J, & Tsang K Y (2012) Cancers (Basel) 4, 1333-1348.
20. Ngiow S F, Teng M W, & Smyth M J (2013) Trends Immunol 34, 548-555.
21. Cua D J, Sherlock J, Chen Y, Murphy C A, Joyce B, Seymour B, Lucian L, To W, Kwan S, Churakova T, et al. (2003) Nature 421, 744-748.
22. Selleck W A, Canfield S E, Hassen W A, Meseck M, Kuzmin A I, Eisensmith R C, Chen S H, & Hall S J (2003) Mol Ther 7, 185-192.
23. Garcia-Tunon I, Ricote M, Ruiz A A, Fraile B, Paniagua R, & Royuela M (2007) BMC Cancer 7, 158.
24. Wall L, Burke F, Barton C, Smyth J, & Balkwill F (2003) Clin Cancer Res 9, 2487-2496.
25. Cherwinski H M, Schumacher J H, Brown K D, & Mosmann T R (1987) J Exp Med 166, 1229-1244.
26. Tripp C S, Wolf S F, & Unanue E R (1993) Proc Natl Acad Sci USA 90, 3725-3729.
27. Fenton M J, Vermeulen M W, Kim S, Burdick M, Strieter R M, & Kornfeld H (1997) Infect Immun 65, 5149-5156.
28. Sharma M, Sharma S, Roy S, Varma S, & Bose M (2007) Immunol Cell Biol 85, 229-237.
29. Rouabhia M, Ross G, Page N, & Chakir J (2002) Infect Immun 70, 7073-7080.
30. Schroder K, Hartzog P J, Ravasi T, & Hume D A (2004) J Leukoc Biol 75, 163-189.
31. Gollob J A, Murphy E A, Mahajan S, Schnipper C P, Ritz J, & Frank D A (1998) Blood 91, 1341-1354.

32. Jana M, Mondal S, Gonzalez F J, & Pahan K (2012) J Biol Chem 287, 34134-34148.
33. Khasnavis S & Pahan K (2014) J Neuroimmune Pharmacol 9, 569-581.
34. Ghosh A, Roy A, Liu X, Kordower J H, Mufson E J, Hartley D M, Ghosh S, Mosley R L, Gendelman H E, & Pahan K (2007) Proc Natl Acad Sci USA 104, 18754-18759.
35. Corbett G T, Roy A, & Pahan K (2012) J Immunol 189, 1002-1013.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A method for treating a cancer, the method comprising administering to a subject in need of such treatment a composition comprising a therapeutically effective amount of an antibody against p40 monomer or an immunologically active fragment thereof, wherein the antibody against p40 monomer comprises mAb a3-3a, mAb a3-7g or an immunologically active fragment thereof, the immunologically active fragment comprising a p40 monomer epitope-binding antibody fragment, wherein the cancer exhibits overexpression of p40 monomer.

2. The method of claim 1, wherein antibody or immunologically active fragment thereof suppresses inhibition of IL-12 signaling.

3. The method of claim 1, wherein the antibody or immunologically active fragment thereof upregulates production of IFN-γ.

4. The method of claim 1, wherein the antibody against p40 monomer or an immunologically active fragment thereof is selected from the group consisting of polyclonal, monoclonal, human, humanized, and chimeric antibodies; and single chain antibodies.

5. The method of claim 1, wherein the antibody or immunologically active fragment thereof does not significantly neutralize action of p40 homodimer.

6. The method of claim 1, wherein the cancer is selected from the group consisting of prostate cancer, breast cancer and liver cancer.

7. The method of claim 1, wherein the composition further comprises at least one pharmaceutically acceptable carrier.

8. The method of claim 1, wherein the subject is a human subject.

9. The method of claim 1, wherein the antibody or immunologically active fragment thereof at least reduces the internalization of IL-12Rβ1 via a caveolin-mediated pathway.

10. The method of claim 1, wherein the antibody or immunologically active fragment thereof is a humanized antibody or an immunologically active fragment thereof.

11. The method of claim 1, wherein the composition is administered orally.

12. The method of claim 1, wherein the composition is administered by a route selected from the group consisting of the subcutaneous, intra-articular, intradermal, intravenous, intraperitoneal and intramuscular routes.

13. A method for inducing cell death, the method comprising contacting the cell with an amount of an antibody against p40 monomer or an immunologically active fragment thereof; wherein the amount is an amount sufficient to induce the death of the cell, wherein the antibody against p40 monomer comprises mAb a3-3a, mAb a3-7g or an immunologically active fragment thereof, the immunologically active fragment comprising a p40 monomer epitope-binding antibody fragment, and wherein the cell is a cancer cell exhibiting overexpression of p40 monomer.

14. The method of claim 13, wherein the cancer cell is selected from the group consisting of a prostate cancer cell, a breast cancer cell and a liver cancer cell.

* * * * *

UNITED STATES PATENT AND TRADEMARK OFFICE
CERTIFICATE OF CORRECTION

| | |
|---|---|
| PATENT NO. | : 11,279,754 B2 |
| APPLICATION NO. | : 15/551710 |
| DATED | : March 22, 2022 |
| INVENTOR(S) | : Kalipada Pahan |

It is certified that error appears in the above-identified patent and that said Letters Patent is hereby corrected as shown below:

In the Specification

Column 1, Line 15:
Delete "This invention was made with Government support of Grant Nos. AT006681 and NS083054, awarded by the National Institutes of Health. The Federal Government has certain rights in the invention."
Insert therefore --This invention was made with government support under R01 AT006681 and R01 NS083054 awarded by the National Institutes of Health. The government has certain rights in the invention.--

Signed and Sealed this
Third Day of September, 2024

Katherine Kelly Vidal
*Director of the United States Patent and Trademark Office*